(12) United States Patent
Hall

(10) Patent No.: US 9,868,974 B2
(45) Date of Patent: Jan. 16, 2018

(54) SENSOR DEVICES

(75) Inventor: Geoffrey Frank Hall, Ross-Shire (GB)

(73) Assignee: SureSensors Ltd., Iverness-Shire (GB)

( * ) Notice: Subject to any disclaimer, the term of this patent is extended or adjusted under 35 U.S.C. 154(b) by 0 days.

(21) Appl. No.: 13/387,072

(22) PCT Filed: Jul. 26, 2010

(86) PCT No.: PCT/GB2010/001420
§ 371 (c)(1),
(2), (4) Date: Jan. 25, 2012

(87) PCT Pub. No.: WO2011/012848
PCT Pub. Date: Feb. 3, 2011

(65) Prior Publication Data
US 2012/0135509 A1    May 31, 2012

(30) Foreign Application Priority Data

Jul. 27, 2009  (GB) .................................. 0913015.4
Sep. 12, 2009  (GB) .................................. 0916067.2

(51) Int. Cl.
*C12M 1/40*     (2006.01)
*G01N 27/00*    (2006.01)
(Continued)

(52) U.S. Cl.
CPC ............. *C12Q 1/001* (2013.01); *C12Q 1/006* (2013.01); *G01N 33/558* (2013.01)

(58) Field of Classification Search
CPC ........ C12C 1/001; C12C 1/006; G01N 33/558
(Continued)

(56) References Cited

U.S. PATENT DOCUMENTS 4,136,145 A    1/1979  Fuchs et al.
4,533,629 A    8/1985  Litman et al.
(Continued)

FOREIGN PATENT DOCUMENTS

DE    10025580    12/2001
EP    0253464     1/1988
(Continued)

OTHER PUBLICATIONS

"Overlay." Def. 1, 1.1. Oxford Dictionaries. Web. Mar. 6, 2015. <http://www.oxforddictionaries.com/us/definition/american_english/overlay>.*

(Continued)

*Primary Examiner* — Keith Hendricks
*Assistant Examiner* — Kourtney S Carlson
(74) *Attorney, Agent, or Firm* — Knobbe Martens Olson & Bear, LLP

(57) ABSTRACT

The present invention relates to a sensor device for measuring a level of an analyte of interest in a fluid, such as body fluid (for example blood, plasma, urine, interstitial fluid, saliva), a method of manufacturing a sensor device, a reagent film for use in a sensor, a method of manufacturing a reagent film for use in a sensor, a method of conducting an assay using a sensor, a method of calibrating a measurement from a sensor, a method of calibrating a batch of sensors, a meter for use with a sensor and a kit comprising a meter and a sensor according to the invention. A first aspect of the invention provides a sensor device for measuring a level of an analyte of interest In a fluid comprising: a flowpath for the fluid; on the flowpath, a reagent for the analyte of interest adjacent to an internal standard comprising a first predetermined amount of a first calibration analyte; and further wherein the reagent and the predetermined amount of a first calibration analyte are in dry form. A second aspect of the (Continued)

invention provides a device comprising: a first calibration electrode having the first predetermined amount of first calibration analyte and reagent for the analyte of interest located thereon; a first working electrode having reagent for the analyte of interest thereon, and further wherein the first calibration electrode lies upstream of the first working electrode.

31 Claims, 19 Drawing Sheets

(51) Int. Cl.
*C12Q 1/00* (2006.01)
*G01N 33/558* (2006.01)

(58) Field of Classification Search
USPC .... 204/403.01–403.15; 205/777.5, 778, 787, 205/792; 435/287.1, 287.6
See application file for complete search history.

(56) References Cited

U.S. PATENT DOCUMENTS

| | | | |
|---|---|---|---|
| 4,774,192 A * | 9/1988 | Terminiello et al. | 436/530 |
| 5,149,622 A | 9/1992 | Brown et al. | |
| 5,272,191 A | 12/1993 | Ibrahim et al. | |
| 5,288,636 A | 2/1994 | Pollmann et al. | |
| 5,393,528 A | 2/1995 | Staab | |
| 5,582,697 A | 12/1996 | Ikeda et al. | |
| 5,628,890 A | 5/1997 | Carter et al. | |
| 5,726,064 A | 3/1998 | Robinson et al. | |
| 5,753,517 A | 5/1998 | Brooks et al. | |
| 5,948,430 A | 9/1999 | Zerbe et al. | |
| 6,193,873 B1 | 2/2001 | Ohara et al. | |
| 6,241,862 B1 | 6/2001 | McAleer et al. | |
| 6,284,125 B1 | 9/2001 | Hodges et al. | |
| 6,284,264 B1 | 9/2001 | Zerbe et al. | |
| 6,419,903 B1 | 7/2002 | Xu et al. | |
| 6,541,030 B2 | 4/2003 | Vaghefi | |
| 6,555,061 B1 | 4/2003 | Leong et al. | |
| 7,276,147 B2 | 10/2007 | Wilsey | |
| 7,470,397 B2 | 12/2008 | Meathrel et al. | |
| 7,548,773 B2 * | 6/2009 | Noble | 600/347 |
| 2003/0053962 A1 | 3/2003 | Zerbe et al. | |
| 2003/0099690 A1 | 5/2003 | Awamura et al. | |
| 2003/0116447 A1 | 6/2003 | Surridge et al. | |
| 2003/0178322 A1 | 9/2003 | Iyengar et al. | |
| 2004/0238359 A1* | 12/2004 | Ikeda | C12Q 1/004 204/403.1 |
| 2005/0123441 A1 | 6/2005 | Unkrig et al. | |
| 2005/0123443 A1 | 6/2005 | Fujiwara et al. | |
| 2005/0196747 A1 | 9/2005 | Stiene | |
| 2006/0024835 A1 | 2/2006 | Matzinger | |
| 2007/0110799 A1 | 5/2007 | Leferve et al. | |
| 2007/0287191 A1 | 12/2007 | Steine et al. | |
| 2008/0149480 A1* | 6/2008 | Bell | 204/403.14 |
| 2008/0152761 A1 | 6/2008 | Shen et al. | |
| 2008/0286359 A1 | 11/2008 | Dansereau et al. | |
| 2008/0289749 A1 | 11/2008 | Charlton et al. | |
| 2008/0299005 A1 | 12/2008 | Meathrel et al. | |
| 2009/0142850 A1 | 6/2009 | Meathrel et al. | |
| 2009/0159442 A1* | 6/2009 | Collier et al. | 204/403.1 |
| 2009/0177406 A1 | 7/2009 | Wu | |
| 2009/0184004 A1 | 7/2009 | Chatelier et al. | |

FOREIGN PATENT DOCUMENTS

| | | |
|---|---|---|
| EP | 0171150 | 2/1998 |
| FR | 2788856 | 1/1999 |
| WO | WO 9119196 | 12/1991 |
| WO | WO 93/15651 | 8/1993 |
| WO | WO 97/18465 | 5/1997 |
| WO | WO 97/38126 | 10/1997 |
| WO | WO 0009999 | 2/2000 |
| WO | WO 01/73109 | 3/2001 |
| WO | WO 01/73124 | 10/2001 |
| WO | WO 02/08763 | 1/2002 |
| WO | WO 03/025573 | 3/2003 |
| WO | WO 03/091717 | 11/2003 |
| WO | WO 2004/000235 | 12/2003 |
| WO | WO 2004/040290 | 5/2004 |
| WO | WO 2004/058217 | 7/2004 |
| WO | WO 2004/071402 | 8/2004 |
| WO | WO 2005/025634 | 3/2005 |
| WO | WO 2005/039499 | 5/2005 |
| WO | WO 2005/040228 | 5/2005 |
| WO | WO 2005/057168 | 6/2005 |
| WO | WO 2005/078118 | 8/2005 |
| WO | WO 2005/080970 | 9/2005 |
| WO | WO 2006/007726 | 1/2006 |
| WO | WO 2006/015615 | 2/2006 |
| WO | WO 2006/067424 | 6/2006 |
| WO | WO 2008/029110 | 3/2008 |
| WO | WO 2008/036516 | 3/2008 |
| WO | WO 2009/018503 | 2/2009 |
| WO | WO2009/048924 | 4/2009 |
| WO | WO 2011/138592 | 11/2011 |

OTHER PUBLICATIONS

Verkouteren et al. "Inkjet Metrology: High-Accuracy Mass Measurements of Microdroplets Produced by aDrop-on-Demand Dispenser", Analytical Chemistry, vol. 81, No. 20, Oct. 15, 2009, pp. 8577-8584.

Meathrel & Moritz, "Dissolvable Films and their Potential in IVDs," IVD Technology Magazine, vol. 13, No. 9, pp. 53-58, Nov./Dec. 2007.

* cited by examiner

Plot of currents measured at a single detection area with no additional dose of glucose on the detection area surface. Plots are shown at various levels of glucose in a buffer sample.

Plot of current measured at different detection areas (E1 – E4).
E3 has a dose of glucose ink-jet printed on it and dried prior to strip assembly.
The sample solution was buffer containing no glucose.

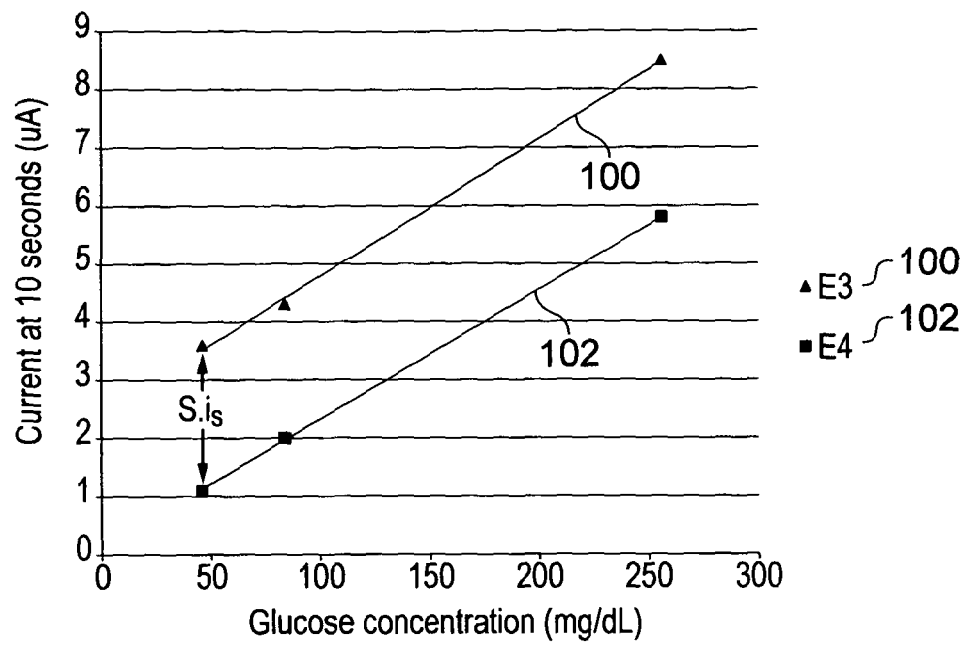

Plot showing the current at 10 seconds as measured on a detection area with no dosed glucose (E4) and a detection area with additional dosed glucose (E3) at three different levels of control solution.

FIG. 18A

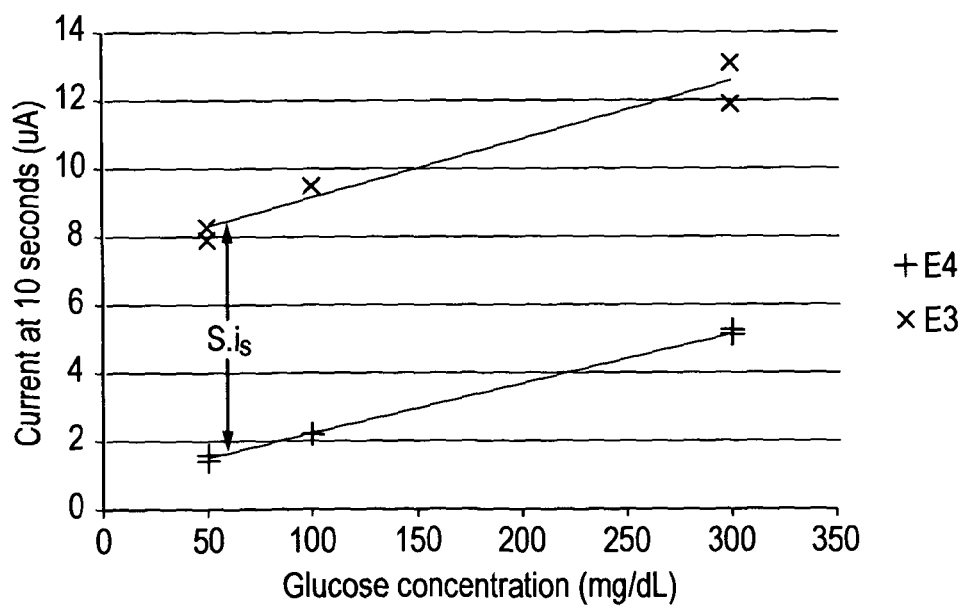

Plot showing the current at 10 seconds as measured on a detection area with no dosed glucose (E4) and a detection area with additional dosed glucose (E3) at three different levels of glucose in whole fingerstick blood (2 reps at each level).

FIG. 18B

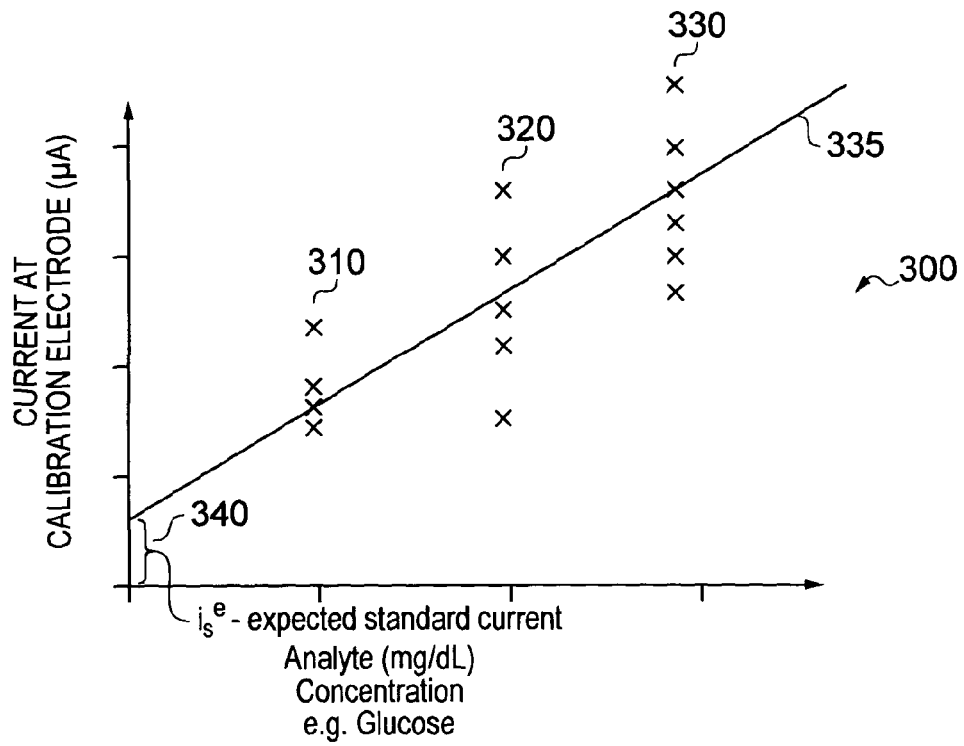

FIG. 19C

Repeat for each calibration electrode in a sensor, if more than one (STEP 350)

Using the determined expected (e.g. average) standard current $i_s^e$ and measured calibration current in a further sensor $i_c^2$ to adjust the working electrode current due to sample $i_w^2$ to provide a corrected working delectrode current $i_m^2$ (STEP 360)

Using a calibration curve (e.g. y=mx+c) to derive an analyte concentration from the corrected working electrode current $i_m^2$ (STEP 370)

FIG. 19D

Plot showing the effect of film thickness on the dissolution rate of the active reagents as illustrated by the steepness of the rise in current in the first second of the assay. The sample was buffer with 310 mg/dL glucose. The film thicknesses shown are wet film thickness A variety of sample entry configurations are possible such as:
"Shelf-fill":
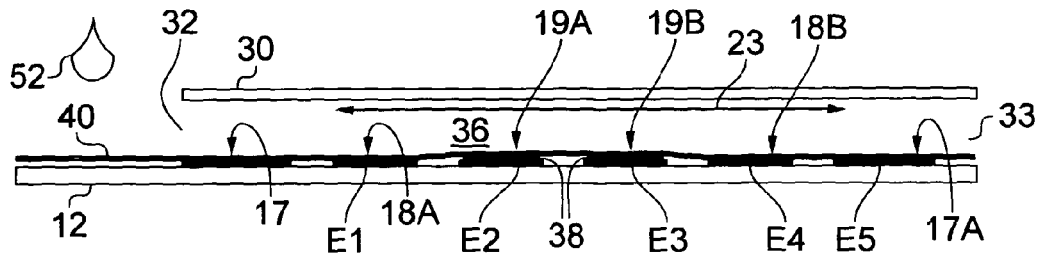
"End-fill": (requires film to be fastened down to prevent sample entering beneath film):
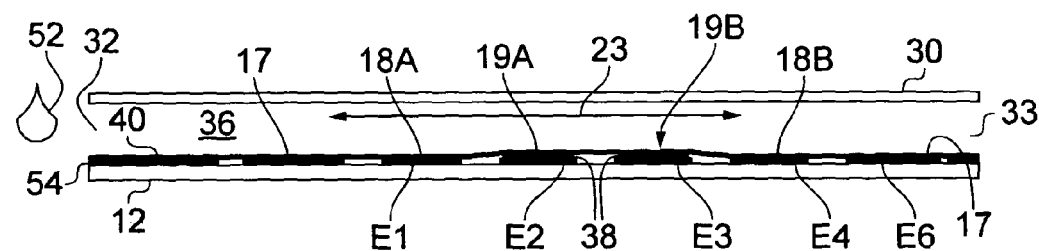
"Hole-fill":
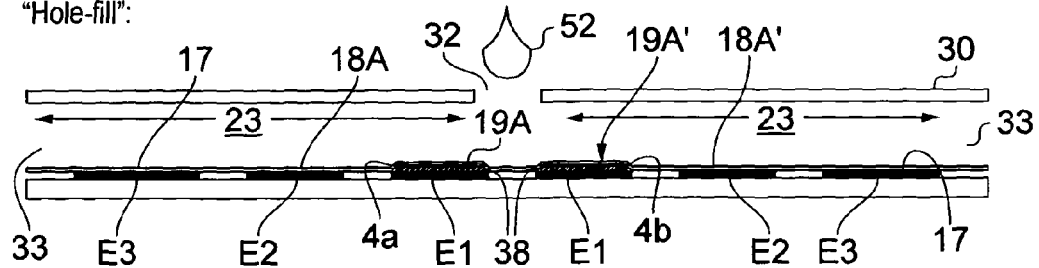
FIG. 23

SENSOR DEVICES

FIELD OF THE INVENTION

The present invention relates to a sensor device for measuring a level such as concentration of an analyte of interest in a fluid, such as body fluid (for example blood, plasma, urine, interstitial fluid, saliva, spinal fluid), a method of manufacturing a sensor device, a reagent film for use in a sensor, a method of manufacturing a reagent film for use in a sensor, a method of conducting an assay using a sensor, a method of calibrating a measurement from a sensor, a method of calibrating a batch of sensors, a meter for use with a sensor and a kit comprising a meter and a sensor according to the invention.

BACKGROUND OF THE INVENTION

The present application is related to and claims priority from UK patent applications GB0913015.4 (SURESENSORS) and GB0916067.2 (SURESENSORS) filed on 27 Jul. 2009 and 12 Sep. 2009 respectively.

Diabetes is one of the most widespread non-infectious diseases. It is estimated that around 246 million people suffer from diabetes and that each year another 7 million people develop the disease. The complications associated with diabetes include an increased risk of suffering a heart attack, stroke, blood circulation disorders, kidney damage, blindness and nerve conduction disorders.

Assessing the concentration of glucose in the blood is an established and effective way of managing diabetes. Diabetics, in particular insulin-dependent diabetics, are advised to monitor their blood glucose levels several times a day in order to adapt and improve treatment plans. Due to the number of times blood glucose levels should be measured, it is highly preferable that diabetics are able to self monitor blood glucose levels without the need for medical supervision.

Home-use assay systems such as those for the monitoring of blood glucose have made significant advances in recent years to reduce the sample volume and assay time. However, it is still possible to get significantly erroneous results due to a wide range of reasons. These reasons include incorrect strip storage, environmental factors, interfering factors in the sample and/or unusually high or low haematocrit levels. The problem is exaggerated if more than one of these factors happens to be present at the time of testing. One solution that manufactures are pursuing is to try to measure in a separate test one or more of the factors that can affect strip response and then correct for any extreme in the measured factor. This method relies on accurate measurement of the factors inducing error and a universally applicable algorithm for error correction.

US2009/0177406 (BAYER; HUAN-PING discloses a biosensor system capable of adjusting a correlation for determining analyte concentration from output signals form one or more index functions extracted from the output signals.

Disposable electrochemical glucose sensors have been available for many years and are described in numerous patents including U.S. Pat. No. 5,288,636 (POLLMANN et al), WO01/073124 (INVERNESS MEDICAL; DAVIES et al.) and U.S. Pat. No. 7,276,147 (ROCHE; WILSEY), U.S. Pat. No. 6,284,125 (USF FILTRATION; HODGES et Al.); WO97/18465 (MEMTEC; HODGES et al.), U.S. Pat. No. 6,241,862 (INVERNESS MEDICAL; McALEER et al.) and U.S. Pat. No. 6,193,873 (LIFESCAN; OHARA et al.). These systems typically use a disposable test sensor, for example in the form a strip that is inserted into a meter. Once a measurement has been carried out the test strip is removed and thrown away. In other words this is a single use disposable sensor. However the currently available systems are all prone to give erroneous results when used near the extremes of more than one of their stated operating ranges (for example with a sample at the low end of the haematocrit range and with an unusually high level of an interfering substance) or when misused in some way. It is known that some users store strips outside of the original packaging resulting in inaccurate readings. One means of mitigating these occurrences and therefore creating a more reliable measurement is the use of an internal calibration that looks for a known reading from an internal standard included in each test strip. This approach has been described in WO 2005/080970 (PA CONSULTING; NOBLE), WO2008/029110 (SURESENSORS; DAVIES) and US2007/0287191 and WO2006/015615 (both from EGOMEDICAL; STEINE et al) for example.

Sensor designs sometimes use water-insoluble membranes to retain reagents at the electrode surface or to provide a barrier to potential interferents (e.g. WO93/15651 ELI LILLY; ALLEN). WO93/15651 (ELI LILLY; ALLEN) discloses "acrylic copolymer membranes for biosensors" where "the membranes of the invention show good adhesion to substrates in an aqueous environment and possess excellent wet-strength."

US2003/0178322 (AGAMATRIX; IYENGAR et al.) discloses the use of a variable potential waveform that is applied to the test strip and signal analysis used to try to determine the effects of interfering factors as opposed to the glucose response. US2009/0184004 (LIFESCAN; CHATALIER et al.) discloses the use of resistance as an indicator of haematocrit and the use of an algorithm to try to correct for the effects of haematocrit.

WO97/38126 (MERCURY DIAGNOSIS; DOUGLAS et al.) discloses a glucose test strip containing " . . . a water insoluble polymeric layer capable of blocking the passage of red blood cells and allowing the passage of blood fluids containing an analyte . . . ."

An alternative use for membranes in diagnostic devices is the use of porous membranes to increase the surface area available to support immobilised or adsorbed reagent. For example WO02/08763 (USF FILTRATION; HODGES et al.) discloses the use of macroporous membranes for immunosensors and also discloses that "The protein or antibody may be contained within a matrix, e.g. polyvinyl acetate. By varying the solubility characteristics of the matrix in the sample, controlled release of the protein or antibody into the sample may be achieved. The support structures described are insoluble or very poorly soluble in water.

The use of a blood cell or interferent exclusion membrane as typically used in biosensors requires that they remain intact in the presence of an aqueous sample.

Electrochemical glucose strips are typically constructed by coating one or more of the detection surfaces with the reagent. In addition to the active ingredients of enzyme and mediator the reagent formulation typically also contains non-reactive ingredients that confer properties required for the manufacturing method or confer desirable properties to the test strip. Typically sensors are made by depositing the reagents onto the detection surface as a liquid and subsequently drying the reagent layer. Deposition of the liquid reagent can be done by a variety of methods such as screen-printing, single drop liquid dosing or ink-jet printing.

US2003/116447 (SURRIDGE et al) discloses the use of an interdigitated array disposed on a flexible substrate and states that "A preferred method for applying the chemistry matrix to the sensor chamber (IDA) is a discrete dispense of 500 nanoliters of the coating solution into the 1 millimeter×4 millimeter chamber . . . ".

U.S. Pat. No. 5,288,636 (POLLMAN et al.) also discloses "6 μl of reagent made by the above protocol is added to well 9 formed by cutout 8. This amount of reagent 11 will substantially cover surface areas 10 on both electrodes . . . ."

The use of disintegratable films for diagnostic devices has been disclosed in WO2005/040228 (ADHESIVES RESEARCH; MEATHREL et al.) in which it is stated that "A disintegratable film containing one or more reagents can improve the stability of the reagents. Additionally, the reagents can be used more effectively and efficiently, since the film can be localized to a particular area within the testing device and can be handled easily as compared to an aqueous solution. Further, providing reagents in film form promotes efficient use and minimises reagent wastage since film can be divided into individual segments having a desired amount of reagent and the need for spraying, coating, or striping a reagent can thus be eliminated, if desired."

WO2005/080970 (PA CONSULTING; NOBLE) discloses a concept with a specific sequence of the detection areas in the flow path. "In a preferred arrangement, the detector means includes at least two detectors, a first of said detectors being arranged to detect the analyte level in the unadulterated sample, and a second of said detectors being arranged downstream of said predetermined amount of the analyte to detect the analyte level in the calibration sample. In one embodiment of the above arrangement, said first and said second detectors are arranged in series on the flow path, and said predetermined amount of the analyte is located between said first and second detectors. Thus there may be a single flow path with the fluid passing, in order, the first detector, the predetermined amount of the analyte and the second detector." It goes on to add "it is also preferable that the calibration glucose on the sensor strip mixes quickly and homogeneously with the blood sample which passes it."

WO2008/029110 (SURESENSORS; DAVIES) discloses the use of multiple internal standards but does not disclose a practical means of designing an electrochemical test strip WO 2006/015615 (EGOMEDICAL; STIENE et al.) discloses a diagnostic device that contains multiple internal standards each within separate sample channels. The predetermined amount of analyte used as the standard is positioned on the opposite face of the sample chamber to the active reagents. This achieves appropriate separation of internal standard analyte from the reagent(s) however creates substantially different transport paths for the analyte from the sample that reacts with the reagent(s) (which will react very close to the working electrode providing very short diffusion paths) as opposed to that from the internal standard which will not react until it meets reagent(s) perhaps somewhere in the bulk sample.

US2006/0024835 (LIFESCAN; MATZINGER) discloses a photometric glucose measurement system that uses reagents spread onto an insoluble support matrix. These insoluble matrices slow down diffusion of reagents and lead to slow assay times of 45 seconds. Such assay times are now commercially unacceptable when compared to the current industry norm of about 5 seconds. The present invention is designed in one exemplary embodiment to achieve rapid test times of less than 10 seconds in an electrochemical assay format.

WO2005/080970 (PA CONSULTING: NOBLE), WO2008/029110 (SURESENSORS; DAVIES), WO2006/015615 (EGOMEDICAL; STIENE et al.) and US2006/0024835 (LIFESCAN; MATZINGER) disclose aspects of the internal standard idea applied to diagnostic test strips. However, these all provide only partial solutions or solutions that have some important disadvantages in the implementation of the internal standard method compared to the present invention.

The art disclosed above does not address issues of provision of an internal standard addressed by one or more embodiments of the present invention. The analyte, glucose in one example, is already dissolved in the test sample and so the reactive ingredients of the test strip are solubilised into the sample already containing the analyte. The inventor has appreciated that the situation with the internal standard test is different in that there is a quantity of analyte in the sample plus an additional 'standard' level of the same analyte that must dissolve into the sample before being measured. Preferably this extra step has no effect on the measurement efficiency of the standard.

Typically sensor production methods deposit a wet reagent formulation onto a detection area by means of wet film casting, liquid dosing or screen printing techniques. If this wet reagent formulation contacts the standard then there is the likelihood that some initial reaction occurs with the internal standard analyte while the reagent layer is drying. This is undesirable as it creates variation that would be detrimental to the use of an internal standard.

A method of manufacturing a sensor having a reagent and internal calibration standard therein is required that reduces and perhaps eliminates to any appreciable extent the risk of any unintended reaction taking place during sensor production and/or later during sensor storage prior to use.

One or more aspects of the invention seek to provide a solution to the problem of unintended reaction between the reagent and the standard dose of calibration analyte, especially when the analyte of interest is the same as the calibration analyte.

One or more aspects of the invention seek a solution to the problem of separating the internal standard and the reagent without introducing differences in their respective transport paths to a measurement electrode.

Further, one or more aspects of the invention seeks a solution to the problem of timing of the reaction between the analyte of interest and the reagent, and timing of the reaction between the reagent and the calibration analyte Such problems may include starting at different times or being of different duration, and perhaps adversely affecting the measurement of the analyte of interest.

The invention also seeks to provide a sensor having small sample volumes and short test times.

SUMMARY OF THE INVENTION

A first aspect of the invention provides a sensor device for measuring a level of an analyte of interest in a fluid comprising: a flowpath for a fluid; on the flowpath, a reagent for the analyte of interest adjacent to an internal standard comprising a first predetermined amount of a first calibration analyte; and further wherein the reagent and the predetermined amount of a first calibration analyte are in dry form.

A second aspect of the invention provides a device comprising: a first calibration electrode having the first predetermined amount of first calibration analyte and reagent for the analyte of interest located thereon; a first working electrode having reagent for the analyte of interest thereon, and further wherein the first calibration electrode lies upstream of the first working electrode.

One or more features in any one or more of the following exemplary embodiments may be combined with any one or more aspects of the present invention.

In an exemplary embodiment the device comprises a test strip which may be a disposable test strip. In an exemplary embodiments one or more measurement electrodes is provided.

In an exemplary embodiment, the first calibration analyte and the analyte of interest are the same analyte. In an exemplary embodiment the reagent is pre-formed in dry form. In an exemplary embodiment the reagent comprises a dry film. In an exemplary embodiment the reagent comprises a water soluble dry film. In an exemplary embodiment the reagent and first pre-determined calibration analyte are not attached.

In an exemplary embodiment the reagent and first predetermined amount of first calibration analyte are on the same side of the flowpath. In an exemplary embodiment, the reagent and the first predetermined amount of calibration analyte are on the same side of a sample chamber, and may be on the same surface of the sample chamber. In an exemplary embodiment on the flowpath there is provided a measurement electrode adjacent to the reagent and adjacent to the predetermined amount of first calibration analyte. In an exemplary embodiment the measurement electrode, the reagent and the first predetermined amount of first calibration analyte are on the same side of the flowpath. In an exemplary embodiment at least part of the reagent and at least part of the predetermined amount of first calibration analyte are between at least part of the measurement electrode and the flowpath. Thus, when fluid flows along the flowpath, or when the sample chamber is full, the reagent and calibration analyte are between the measurement electrode and the bulk of the sample fluid.

In an exemplary embodiment the reagent is adjacent to the predetermined amount of first calibration analyte so that a wave front of fluid flowing along the flow path arrives at the reagent for the analyte of interest and at the first predetermined amount of a first calibration analyte at approximately the same time. In an exemplary embodiment the wave front arrives at the reagent for the analyte of interest and at the first predetermined amount of a first calibration analyte within a time selected from the group of about 0.75 s, about 0.5 s, about 0.25 s, about 0.2 s, about 0.1 s, about 0.05 s, about 0.025 s, about 0.02 s, about 0.01 s. In an exemplary embodiment a reagent film is provided and the reagent film has a dissolution rate so that more than half of the film or more than 75% of the film or more than about 90% of the film, within a given area, has dissolved within a time selected from the group of: about 2 s, less than about 2 s, about 1.5 s, less than about 1.5 s, about 1 s, less than about 1 s, about 0.5 s, less than about 0.5 s, about 0.25 s, less than about 0.25 s, less than about 0.2 s, less than about 0.1 s. In an exemplary embodiment the reagent is located adjacent to the predetermined amount of first calibration analyte within a distance of zero µm (when touching) or on the order of units or tens of µm, or within about 5 to 15 µm, or within about 10 µm, or within about 5 µm of one another. In an exemplary embodiment one or both of the reagent and the predetermined amount of first calibration analyte are located adjacent to the measurement within a distance of zero µm (when touching) or on the order of units or tens of µm, or within about 5 to 15 µm, or within about 10 µm, or within about 5 µm of one another. In an exemplary embodiment one measurement electrode is separated from a neighbouring measurement electrode by a distance of about 100 µm to about 300 µm or about 100 µm to about 200 µm. In an exemplary embodiment the flow path comprises a capillary channel for drawing fluid there along by capillary action.

In an exemplary embodiment the device comprises: a conductive layer comprising at least one measurement electrode; a calibration layer comprising at least the first predetermined amount of the first calibration analyte; the first predetermined amount of the first calibration analyte located on at least part of the measurement electrode; the reagent for the analyte of interest located on at least part of the measurement electrode having the first predetermined amount of calibration analyte thereon to form a calibration electrode. One or more calibration layers may be provided.

In an exemplary embodiment the reagent for the analyte of interest overlays at least part of the first predetermined amount of first calibration analyte on the calibration electrode. In an exemplary embodiment the reagent is in the form of a water soluble dry film, and the water soluble dry film overlays at least part of the calibration layer and/or the conductive layer to form a reagent layer. In an exemplary embodiment the device comprises a conductive layer comprising at least two electrodes; a calibration layer comprising at least the first predetermined amount of the first calibration analyte located on one of the at least two electrodes, leaving the other electrode free from calibration analyte; a reagent layer comprising the reagent for the analyte of interest, the reagent layer overlaying at least part of each of the at least two electrodes forming a working electrode free from calibration analyte having reagent thereon and a calibration electrode having the first predetermined amount of the first calibration analyte and reagent thereon. In an exemplary embodiment the reagent layer overlays at least part of the first predetermined amount of first calibration analyte. In an exemplary embodiment the calibration analyte is located on an uppermost surface of a measurement electrode. In an exemplary embodiment the calibration analyte is located adjacent the measurement electrode before the reagent is located adjacent the measurement electrode. In an exemplary embodiment the calibration analyte is deposited by a wet deposition technique and subsequently dried. In an exemplary embodiment the calibration analyte is deposited by ink jet printing.

In an exemplary embodiment the device comprises; three or more measurement electrodes, at least one electrode having the predetermined amount of first calibration analyte and the reagent for the analyte of interest thereon to form a calibration electrode, at least one electrode free from calibration analyte having the reagent for the analyte of interest thereon to form a working electrode, and at least one electrode free from calibration analyte and having reagent for the analyte of interest thereon to form a counter/reference electrode. In an exemplary embodiment a further electrode is provided free from calibration analyte and free from reagent to form a background electrode. In an exemplary embodiment no reagent is present or reagent free from active ingredient is present.

In an exemplary embodiment a single flow path is provided or a single linear flowpath is provided. In an exemplary embodiment all the measurement electrodes are on the same flowpath.

In an exemplary embodiment the device comprises a first calibration electrode having the first predetermined amount of first calibration analyte and reagent for the analyte of interest located thereon; and a second calibration electrode having either a second predetermined amount of a first calibration analyte or a first predetermined amount of a second calibration analyte and reagent for the analyte of interest located thereon. In an exemplary embodiment the device comprises three or more calibration electrodes having either the same or different amounts of the same or different calibration analytes and reagent for the analyte of interest located thereon. In an exemplary embodiment at least one of the calibration analytes is the same analyte as the analyte of interest. In an exemplary embodiment at least two working electrodes having reagent thereon are provided.

In an exemplary embodiment one or more of the following: geometry of the flow path, height of the flowpath, width of the flowpath, length of the flowpath, location along the flowpath of at least the first calibration electrode, location along the flowpath of at least the first working electrode, distance between the first calibration electrode and the first working electrode, dissolution rate of the reagent, dissolution rate of the first predetermined amount of the first calibration analyte, thickness of the reagent, thickness of the reagent film when provided are selected so that a suitable measurement indicative of the concentration of the analyte of interest can be taken at the first working electrode before calibration analyte or reaction products from the first calibration electrode can travel by diffusion or otherwise from the first calibration electrode to the first working electrode.

In an exemplary embodiment the assay time for a measurement at least one measurement electrode is less than the time taken for diffusion of reagent or reaction products from another measurement electrode. In an exemplary embodiment the assay time at least one working electrode is less than the time taken for the calibration analyte and reagent on the calibration electrode, and/or reaction products therefrom, to dissolve and travel by diffusion or otherwise to that working electrode.

In an exemplary embodiment the analyte of interest is selected from glucose, cholesterol, triglycerides, proteins, lactate, pyruvate, alcohol, uric acid and ketones. In an exemplary embodiment the reagent comprises one or more selected from the group of an enzyme, a mediator, and a co-factor. In an exemplary embodiment the internal standard comprises the first predetermined amount of calibration analyte, a suitable mediator and/or a co-factor and the reagent comprises an enzyme.

In an exemplary embodiment the reagent is in the form of a dry film, the dry film comprising: a first film forming ingredient; a first active ingredient sensitive to the analyte of interest. In an exemplary embodiment the dry film comprises a first film forming ingredient selected from the group of a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose. In an exemplary embodiment the dry film further comprises a second film forming ingredient selected from a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose.

In an exemplary embodiment the device comprises a first film forming ingredient and a second film forming ingredient; the second film forming ingredient having better dissolution and less hydrophobic properties than the first film forming ingredient. In an exemplary embodiment the dry film comprises a buffer.

In an exemplary embodiment the reagent comprises at least first and second active ingredients sensitive to the analyte of interest. In an exemplary embodiment the second active ingredient is a mediator or potassium ferricyanide mediator. In an exemplary embodiment the first active ingredient is an enzyme or glucose oxidase enzyme or glucose dehydrogenase enzyme.

In an exemplary embodiment the device comprises at least one further film ingredient selected from the group of plasticizers, disintegrants, and surfactants.

In an exemplary embodiment at least one further film ingredient is selected from the group of plasticizers: xylitol, sorbitol, erythritol, polyethylene glycol. In an exemplary embodiment at least one further film ingredient is selected from the group of disintegrants: microcrystalline cellulose, sodium croscarmellose, sodium starch glycate and Prosolv SMCC®. In an exemplary embodiment at least one further film ingredient is selected from the group of surfactants: flurosurfactants, Zonyl® FSN-10©, silicone polyether copolymers, Dow Corning® 193C, Triton® X-100.

In an exemplary embodiment the device comprises a fluid chamber formed by at least one side wall and/or lid, the fluid chamber being sized and/or shaped and/or of dimensions and/or treated so as to act as a capillary for drawing fluid therethough along the flowpath. In an exemplary embodiment the device comprises a generally rectangular substrate having two long edges and two short edges and a fluid entrance to the flow path is provided at one of the following: at or adjacent a long edge; at or adjacent a short edge; in a chamber lid of the device. In an exemplary embodiment the device comprises a substrate and in which the reagent film forming a reagent layer extends to an edge of the substrate and a chamber lid is provided which does not extend to said edge so as to form a shelf region of exposed reagent film, and the entrance to the flow path is adjacent to shelf region of exposed of the reagent film.

In a further aspect there is provided a sensor device for measuring a level of an analyte of interest in a fluid comprising: a flowpath for the fluid; on the flowpath, a reagent for the analyte of interest adjacent to an internal standard comprising a first predetermined amount of a first calibration analyte; and further wherein the reagent and the predetermined amount of a first calibration analyte are in dry form; and the reagent is pre-formed in dry form.

In a further aspect there is provided a sensor device for measuring a level of an analyte of interest in a fluid comprising: a flowpath for the fluid; on the flowpath, a reagent for the analyte of interest adjacent to an internal standard comprising a first predetermined amount of a first calibration analyte; wherein the reagent and the predetermined amount of a first calibration analyte are in dry form, and wherein the reagent and first predetermined amount of first calibration analyte are on the same side of the flowpath.

In a further aspect there is provided a sensor device for measuring a level of an analyte of interest in a fluid comprising: a flowpath for the fluid; on the flowpath, a reagent for the analyte of interest and an internal standard comprising a first predetermined amount of a first calibration analyte; wherein the reagent and the predetermined amount of a first calibration analyte are in dry form and the reagent comprises a water soluble dry film.

In a further aspect of the invention there is provided a method of manufacturing a sensor device for detecting an analyte of interest comprising: forming a flow path, placing on the flow path, a reagent for the analyte of interest adjacent to a first predetermined amount of a first calibration analyte and further wherein the reagent and the predetermined amount of a first calibration analyte are in dry form.

In an exemplary embodiment the method comprises placing a measurement electrode on the flowpath and placing the reagent and the first predetermined amount of a first calibration analyte adjacent to the measurement electrode.

In an exemplary embodiment the first calibration analyte and the analyte of interest are the same analyte. In an exemplary embodiment the reagent is in dry form prior to the step of placing. In an exemplary embodiment the reagent consists of a dry reagent film. In an exemplary embodiment the dry film comprises a water soluble dry reagent film. In an exemplary embodiment the method comprises the step of pre-forming the dry reagent film. In an exemplary embodiment pre-forming comprises providing a first film forming ingredient, adding at least one active ingredient sensitive to the analyte, to the first film forming ingredient to form a mixture, drawing out the mixture to form a film, drying the film, In an exemplary embodiment the method comprises forming a solution and drawing out the solution to form a film.

In an exemplary embodiment the film forming ingredient comprises a polymer. In an exemplary embodiment the method comprises providing a first forming ingredient selected from the group of modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose. In an exemplary embodiment the method comprises providing a second film forming ingredient selected from the group of a first forming ingredient selected from the group of modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxy propyl methyl cellulose. In an exemplary embodiment the method comprises providing a first film forming ingredient and a second film forming ingredient; the second film forming ingredient having better dissolution and less hydrophobic properties than the first film forming ingredient.

In an exemplary embodiment the method comprises providing at least a first and a second active ingredient. In an exemplary embodiment the method comprises providing an enzyme as a first active ingredient and, if provided, a mediator as a second active ingredient and, if provided, a co-factor as a third active ingredient. In an exemplary embodiment the enzyme is glucose oxidase or glucose dehydrogenase and, if provided, the mediator is potassium ferricyanide.

In an exemplary embodiment the method comprises providing at least one further film ingredient selected from the group of plasticizers, disintegrants and surfactants. In an exemplary embodiment the method comprises providing at least one further film ingredient selected from the group of plasticizers: xylitol, sorbitol, erythritol, polyethylene glycol. In an exemplary embodiment the method comprises providing at least one further film ingredient from the group of disintegrants: microcrystalline cellulose, sodium croscarmellose, sodium starch glycate and Prosolv SMCC®. In an exemplary embodiment the method comprises providing at least one further film ingredient selected from the group of surfactants: flurosurfactants, Zonyl® FSN-10©, silicone polyether copolymers, Dow Corning® 193C, Triton® X-100.

In an exemplary embodiment the method comprises providing at least one electrode, placing a predetermined amount of first calibration analyte onto the electrode, placing the reagent for the analyte of interest over the predetermined amount of first calibration analyte to form a calibration electrode. In an exemplary embodiment the reagent comprises a water soluble dry reagent film. In an exemplary embodiment the method comprises forming a conductive layer comprising at least one electrode, forming a first calibration layer comprising at least one predetermined amount of a first calibration analyte on at least one electrode of the electrode layer, pre-forming a reagent film for an analyte of interest, placing the reagent film over at least part of the at least one electrode having the predetermined amount of calibration analyte thereon to form a calibration electrode. In an exemplary embodiment the method comprises placing the reagent film at least partly on or wholly over the predetermined amount of calibration analyte. In an exemplary embodiment the method comprises forming at least two measurement electrodes; leaving at least one measurement electrode free from calibration analyte; placing reagent film over at least part of said at least one measurement electrode to form a working electrode; placing reagent film over at least part of the electrode having calibration analyte thereon to form a calibration electrode.

In an exemplary embodiment the method comprises leaving at least one electrode free from calibration analyte and free from reagent to form a background electrode. This may mean no reagent is present or reagent free from analyte sensitive active ingredient is present.

In an exemplary embodiment the method comprises forming at least one calibration electrode lying upstream of at least one working electrode on the flow path. In an exemplary embodiment a single flow path is provided or a single linear flowpath is provided.

In an exemplary embodiment the method comprises providing a first calibration electrode having the first predetermined amount of first calibration analyte and reagent for the analyte of interest located thereon; and providing a second calibration electrode having either a second predetermined amount of a first calibration analyte or a first predetermined amount of a second calibration analyte and reagent for the analyte of interest located thereon. In an exemplary embodiment the method comprises providing three or more calibration electrodes having either the same or different amounts of the same or different calibration analytes and reagent for the analyte of interest located adjacent thereto, for example thereon. In an exemplary embodiment at least one of the calibration analytes is the same analyte as the analyte of interest.

In an exemplary embodiment the method comprises selecting one or more of the following: geometry of the flow path, height of the flowpath, width of the flowpath, length of the flowpath, location along the flowpath of at least the first calibration electrode, location along the flowpath of at least the first working electrode, distance between the first calibration electrode and the first working electrode, dissolution rate of the reagent, dissolution rate of the first predetermined amount of the first calibration analyte, thickness of the reagent, thickness of the reagent film, if provided, are selected so that, in use, a suitable measurement indicative of the concentration of the analyte of interest can be taken at the first working electrode before calibration analyte or reaction products from the first calibration electrode can travel by diffusion or otherwise from a first calibration electrode to the first working electrode.

In an exemplary embodiment the analyte of interest is selected from glucose, cholesterol, triglycerides lactate, pyruvate, alcohol, uric acid and ketones. In an exemplary embodiment the reagent comprises one or more selected from the group of an enzyme, a mediator, and a co-factor. In an exemplary embodiment the internal standard comprises the first predetermined amount of calibration analyte, a suitable mediator and/or a co-factor and the reagent comprises an enzyme. In an exemplary embodiment the internal standard comprises a buffer.

In a further aspect of the invention there is provided a reagent film comprising: a first film forming ingredient, and a reagent comprising a first active ingredient sensitive to an analyte of interest.

In an exemplary embodiment the reagent film has wet thickness selected from the group of: in the range of about 30 to about 90 μm, in the range of about 40 to about 80 μm, less than about 100 μm, less than about 90 μm, about 90 μm, about 80 μm, less than about 80 μm, about 60 μm, or less than about 60 μm. In an exemplary embodiment the reagent film has a dissolution rate so that more than half of the film or more than 75% of the film or more than about 90% within a given area, has dissolved within a time selected from the group of: about 2 s, less than about 2 s, about 1.5 s, less than about 1.5 s, about 1 s, less than about 1 s, about 0.5 s, less than about 0.5 s, about 0.25 s, less than about 0.25 s, less than about 0.2 s, less than about 0.1 s.

In an exemplary embodiment the reagent film is dry. In an exemplary embodiment the reagent film is water soluble.

In an exemplary embodiment the reagent film comprises a first film forming ingredient selected from the group of a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose. In an exemplary embodiment the reagent film comprises a second film forming ingredient selected from the group of a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose. In an exemplary embodiment the reagent film comprises a first film forming ingredient and a second film forming ingredient; the second film forming ingredient having better dissolution and less hydrophobic properties than the first film forming ingredient.

In an exemplary embodiment the reagent comprises at least first and second active ingredients sensitive to the analyte of interest. In an exemplary embodiment the second active ingredient is a mediator or potassium ferricyanide mediator. In an exemplary embodiment the first active ingredient is an enzyme or glucose oxidase enzyme or glucose dehydrogenase enzyme. In an exemplary embodiment at least one further film ingredient is selected from the group of plasticizers, disintegrants, and surfactants. In an exemplary embodiment at least one further film ingredient is selected from the group of plasticizers: xylitol, sorbitol, erythritol, polyethylene glycol. In an exemplary embodiment at least one further film ingredient is selected from the group of disintegrants: microcrystalline cellulose, sodium croscarmellose, sodium starch glycate and Prosolv SMCC®. In an exemplary embodiment at least one further film forming ingredient is selected from the group of surfactants: flurosurfactants, Zonyl® FSN-10©, silicone polyether copolymers, Dow Corning® 193C, Triton® X-100.

A further aspect of the invention comprises a method of manufacturing a reagent film comprising: providing a first film forming ingredient, adding at least one active ingredient sensitive to the analyte, to the first film forming ingredient to form a mixture, drawing out the mixture to form a film, drying the film.

In an exemplary embodiment the method comprises forming a solution and drawing out the solution to form a film. In an exemplary embodiment the method comprises controlling the wet film thickness. In an exemplary embodiment the method comprises drawing out the film to have a predetermined wet thickness. In an exemplary embodiment the method comprises providing a reagent film having a wet thickness selected from the group of: in the range of about 30 to about 90 μm, in the range of about 40 to about 80 μm, less than about 100 μm, less than about 90 μm, about 90 μm, about 80 μm, less than about 80 μm, about 60 μm, or less than about 60 μm.

A further aspect of the invention comprises a method of conducting an assay using a sensor comprising: taking a measurement indicative of the concentration of the analyte of interest at a first working electrode before calibration analyte or reaction products from the first calibration electrode can travel by diffusion or otherwise from the first calibration electrode to the first working electrode. In an exemplary embodiment an assay time for a measurement at least one measurement electrode is less than the time taken for diffusion of reagent or reaction products from another measurement electrode. In an exemplary embodiment the wave front arrives at both the reagent for the analyte of interest and at the first predetermined amount of a first calibration analyte within a time selected from the group of about 0.75 s, about 0.5 s, about 0.25 s, about 0.2 s, about 0.1 s, about 0.05 s, about 0.025 s, about 0.02 s, about 0.01 s In an exemplary embodiment the method comprises a reagent film and the reagent film has a dissolution rate so that more than about half of the film or more than about 75% of the film or more than about 90% of the film within a given area has dissolved, for example within a body fluid such as blood or plasma, within a time selected from the group of: about 2 s, less than about 2 s, about 1.5 s, less than about 1.5 s, about 1 s, less than about 1 s, about 0.5 s, less than about 0.5 s, about 0.25 s, less than about 0.25 s, less than about 0.2 s, less than about 0.1 s In an exemplary embodiment the method comprises: measuring a signal indicative of analyte concentration before the reaction has reached steady state at a time selected from the group of: between about 4 s to about 12 s, between about 4 s to about 10 s, between about 5 s to about 10 s, between about 4 to about 6 s, at about 5 s, at about 6 s, at about 8 s, at about 10 s, at about 12 s.

A further aspect of the invention provides a method of calibrating a measurement comprising: providing a first sensor according to any embodiment of the first and/or second aspect of the invention; measuring a working electrode current at a working electrode; measuring a calibration current reflective of a predetermined amount of calibration analyte and a current reflective of a known amount of analyte of interest in a fluid sample dosed with analyte; using the calibration current the working electrode current to determine a correction factor. In an exemplary embodiment the method comprises providing a second sensor according to any embodiment of the first and/or second aspect of the invention; applying the correction factor to the working electrode current and calibration current from the second sensor to arrive at a corrected working electrode current and/or a corrected analyte concentration.

In an exemplary embodiment the method comprises: providing a batch of sensors and selecting a subset of sensors from the batch; determining the calibration current and working electrode currents at the same respective measurement electrodes for the same and/or different known amounts of analyte of interest in fluid samples dosed with analyte; determining an expected calibration current for that amount of calibration analyte for that design of sensor; providing a correction factor reflective of the expected calibration current. In an exemplary embodiment the method comprises providing a further sensor from the batch and using a fluid sample having an unknown amount of analyte to conduct a test; using the correction factor to correct the working electrode current and calibration current from the test to provide a corrected working electrode current. In an exemplary embodiment the method comprises determining an expected calibration current for this design of sensor for the first amount of calibration analyte by one or more of: averaging one or more calibration currents from the same or different sensors: fitting a curve or line to a series of calibration currents from the same or different sensors; determining the expected calibration current at sample analyte concentration of zero. In an exemplary embodiment the internal standard calibration method described herein may be used instead of or, more preferably, in addition to known calibration methods for converting a current measurement to a analyte measurement such as that described in relation to FIG. 5.

A further aspect of the invention provides a meter comprising: a connector for connecting to a sensor according to any embodiment of the first and/or second aspects of the invention, a power and measurement circuit for operating the sensor and measuring a measurement signal therefrom, a central processing unit for receiving a measurement signal from the power and measurement unit and for analysing the measurement signals to deliver a measurement result. In an exemplary embodiment the central processing unit is arranged to correct a working electrode current as described herein.

A further aspect of the invention provides a kit comprising: a meter and a sensor according to any embodiment of any aspects of the invention.

BRIEF DESCRIPTION OF THE DRAWINGS

The invention will now be described by way of example only with reference to the following figures in which like reference numerals refer to like features.

FIG. 5 is a schematic plot of measured current against glucose concentration in milligrams per deciliter as measured on YSI (Yellow Springs) instrument or similar.

FIG. 7 shows three cross sectional views of various arrangements of measurement electrodes with respect to the direction of fluid flow.

FIG. 18A shows plots of experimental data of current developed at particular working electrodes (E3 with additional dosed glucose and E4 with no dosed glucose) at 10 seconds versus glucose concentration in milligrams per deciliter using control solution.

FIG. 18B shows plots of experimental data of current developed at particular working electrodes (E3 with additional dosed glucose and E4 with no dosed glucose) at 10 seconds versus glucose concentration in milligrams per deciliter using whole fingerstick blood (2 repetitions at each glucose level). Here the level of dosed glucose is much higher than that used in the experiment in FIG. 18A.

FIG. 19C shows a plot of example data of current developed at a calibration electrode at different levels of known sample analyte concentration in several test sensors of the same design, each having the same predetermined amount of calibration glucose dosed thereon.

FIG. 19D shows optional steps for the methods of FIGS. 19A and 19B.

FIG. 22A shows a five electrode system (one counter/reference and four measurement electrodes), and a side fill flow path extending from one long edge of the generally rectangular sensor to the other long the edge of the generally rectangular sensor.

FIG. 22B shows a five electrode system having a top fill arrangement. In this example, the use of a water-soluble dry film reagent is particularly desirable.

FIG. 22C shows a plan view of a five measurement electrode system having four electrodes for use as enzyme electrodes or calibration electrodes and a single interdigitated counter/reference electrode. Again, a side fill from one longitudinal edge of a generally rectangular strip to the other longitudinal edge is shown.

In FIG. 22D a five measurement electrode system in an alternative arrangement is shown. Here an entrance 32 to flow path 23 is provided along a short edge of a generally rectangular sensor, referred to as an "end fill".

FIG. 23 shows schematic cross sectional views of example sensors according to one or more aspects of the invention. Here shelf fill, end fill and top fill arrangements are shown.

DETAILED DESCRIPTION OF THE DRAWINGS

Figure 1:
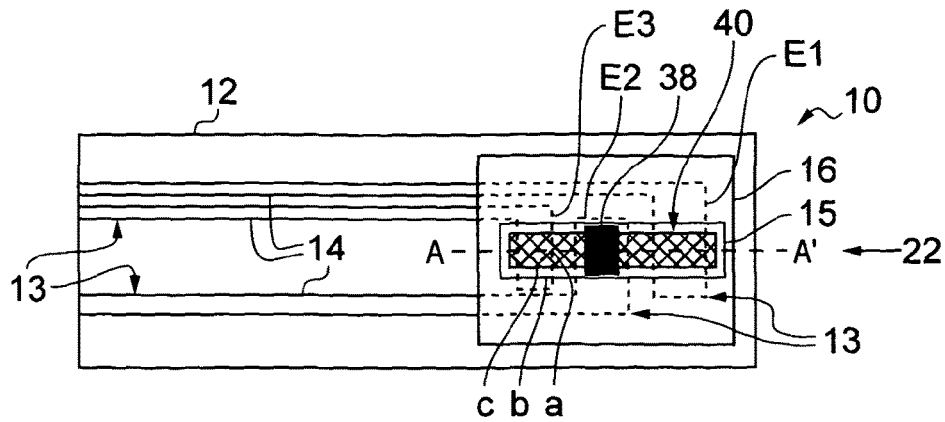
FIG. 1 is a plan view of test sensor device in the form of an electrochemical test strip according to one embodiment of the invention.

Referring now to FIG. 1, there is shown a plan view of a sensor 10 comprising a generally rectangular substrate 12 having conductive tracks 14 laid thereon.

While substrate 12 is generally rectangular in shape, other shapes of sensors such as square, circular, ovoid, oval could be used within this invention. Substrate 12 can be of any suitable material such as polyester or polythene. Conductive tracks 14 lead to measurement electrodes 18. Typically, measurement electrodes and conductive tracks 14 are made from the same material although this need not be the case. Typical materials, as is known to those skilled in the art, may be used include gold, silver, silver/silver chloride, carbon, platinum or palladium. An insulation layer 16, comprising insulation material, overlies at least in part conductive tracks 14 and measurement electrodes E1, E2, E3. Insulation layer 16 has a window 15 positioned therein. Window 15 exposes particular portions of measurement electrodes 18 to form exposed areas of measurement electrodes for detection of analyte within a fluid sample. Insulation layer 16 may be made from inks such as Insulayer™ from Ercon Inc. (Wareham, Mass., USA) or D2071120D1 polymer dielectric from Gwent Electronic Materials Ltd (Pontypool, Gwent UK. Such materials and their use and methods of depositing same are well known in the art. Typically, conductive layers 14 and/or insulation layer 16 may be laid down by screen printing or other methods such as lithographic procedures, inkjeting, sputtering and/or etching.

It is helpful for the optimum performance of the sensor for the exposed area of measurement electrodes 18 to be well-defined. Thus, it is appropriate that the deposition technique selected is suitable to provide a suitable definition of the edges of the measurement electrodes 18. It is therefore desirable if conductive layer 13 is deposited via a technique that provides good edge definition for edges "a" of measurement electrodes 18 and insulation layer 16 is deposited by a technique which provides good definition of edge "b" of measurement electrode 18 i.e. the edge exposed by the insulation window 15.

A water-soluble dry reagent film 40 is provided overlaying two of the measurement electrodes 18. One edge "c" of the water-soluble dry reagent film 40 containing reagent may lie within edge "b" of insulation window 15 as shown in FIG. 1 or it may extend beyond edge "b" of insulation layer window 15 thereby covering all of the exposed area of measurement electrode 18 in that direction. Water-soluble dry reagent film 40 also extends to cover measurement electrodes E1, E2 and E3 to form working electrodes 18, a counter/reference electrode 17 and a calibration electrode 19. A direction of fluid flow 22 is also shown in FIG. 1.

Figure 2:
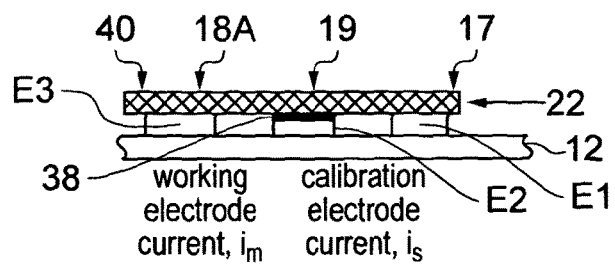
FIG. 2 is a cross sectional view along the line AA' of the sensor of FIG. 1.

Turning now to FIG. 2, a cross-sectional view long line AA' is shown. Here, three measurements electrodes E1, E2 and E3 are shown. A first electrode E1 forms a counter/reference electrode 17 and is exposed first to fluid flowing in direction 22. A second electrode E2 has a predetermined amount of calibration analyte 38 disposed thereon to form a calibration electrode 19. Calibration analyte 38 may be deposited wet and subsequently dried, or may be deposited in dry form. This calibration analyte 38 may be the same or may be different from the analyte of interest for the sensor. A third electrode E3 is also provided to form a working electrode 18. A water soluble dry reagent film 40 is positioned on and overlays, at least in part, the uppermost surfaces of electrodes E1, E2 and E3. Thus, reagent film 40 is adjacent to calibration analyte 38.

Measurement electrode E1 encounters fluid flowing in direction 22 before measurement electrode E2 encounters the wave front from this fluid. Likewise measurement electrode E2 encounters the wave front from fluid flowing along direction 22 before measurement electrode E3. The three electrodes provided have different functions. Measurement electrode E1 functions as a counter/reference electrode 18. Measurement electrode E2 has a predetermined amount of analyte calibration analyte 38 positioned thereon. In addition a water-soluble dry reagent film 40 extends over the uppermost surface of measurement electrode E2. This combination of measurement electrode E2 adjacent to calibration analyte 38 adjacent to reagent, here in the form of reagent film 40, provides a calibration electrode 19. Measurement electrode E3 is also overlaid, at least in part, by water-soluble dry reagent film 40 and thereby forms a first working electrode 18A.

To take a measurement, a voltage, such as +200-600 mv, or more particularly +400 mV, is applied between the working electrode(s) 18A, calibration electrode 19 and counter/reference electrode 17. The current developed at the working electrode and at the calibration electrode 19 is then measured as an indication of the concentration of analyte in the fluid.

Figure 3:
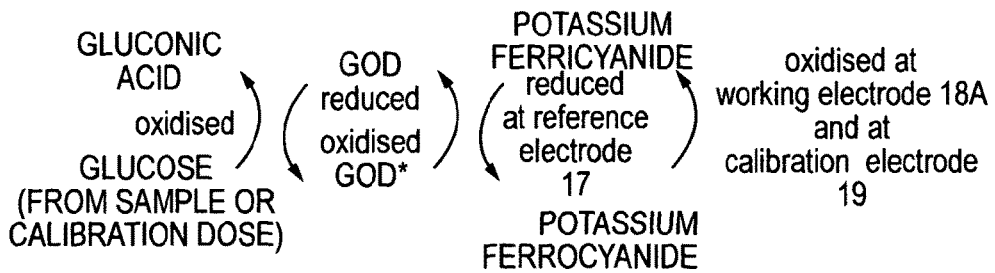
FIG. 3 is as schematic representation of an example reaction regime.
Figure 5:
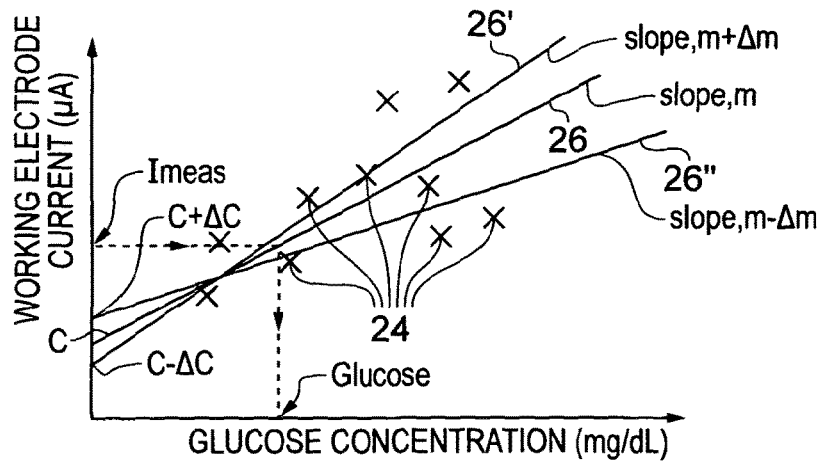
Figure 4:
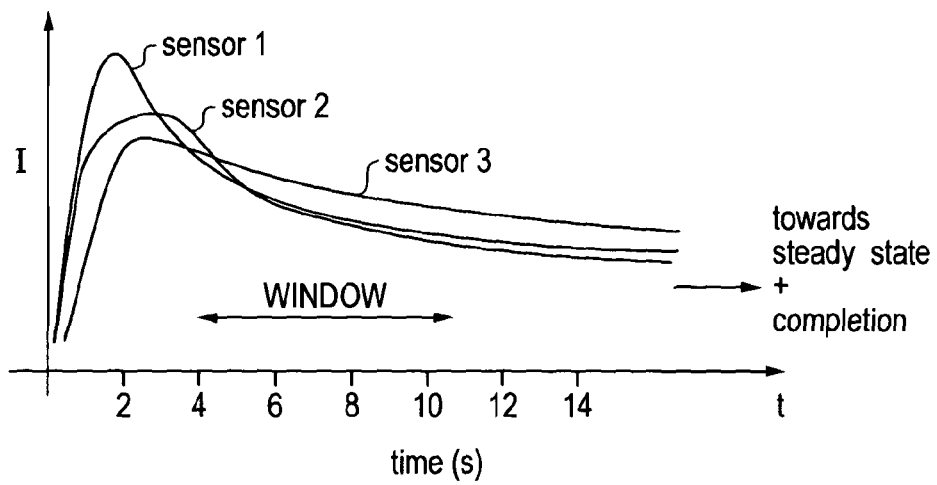
FIG. 4 is an example plot of current against time for three example sensors.

Turning briefly to FIGS. 3, 4 and 5, schematic drawings of a reaction framework, example plots of current with time and an example calibration graph are shown respectively. In FIG. 3, it can be seen that an analyte, here glucose, in the presence of a suitable enzyme and optional mediator (here glucose oxidase and potassium ferricyanide) can be oxidised into gluconic acid. In turn, the glucose oxidase is reduced to its reduced form. Likewise potassium ferricyanide is reduced to potassium ferrocyanide at the counter/reference electrode, whilst the reverse occurs at the working electrode in that potassium ferrocyanide is oxidised to potassium ferricyanide.

For the measurement of glucose, there are two schools of thought regarding the appropriate time to measure the current developed at the working electrode to be suitably indicative of the amount of analyte in the sample. One school of thought leads towards the measurements of the current once the reaction has gone to completion or at least a steady-state has been achieved. Examples of glucose sensors that work in this manner include Freestyle Lite from Abbott Diabetes Care Inc. (Alameda, Calif., USA) or Wavesense Jazz from Agamatrix Inc. (Salem, N.H., USA). Assay times for such sensors are variable rather than fixed and tend to increase for higher glucose levels.

The other school of thought is to take a measurement whilst the reaction is still progressing and yet after such an initial period of time that the number of variables and the varying conditions has settled down enough to enable a measurement to be made. Examples of sensors that work in this manner include One Touch Ultra from Lifescan, Milpitas, Calif. and Accu-Chek Aviva from Roche Diagnostics Inc. (Indianapolis, Ind., USA). As can be seen in FIG. 4, there is a window typically extending from around three to four seconds and upwards to somewhere in the region of ten to 12 or 15 seconds during which measurements can be taken of current at an electrode at a selected point in time and this will be related in a consistent manner to the amount of analyte in the fluid sample. Thus, the amount of glucose in a sample can be related by a simple linear equation ($y=mx+c$) to the current developed at the working electrode after a period of time, say 5 seconds. Nevertheless due to variations in the manufacturing process, manufacturing ingredients and so on, this relationship can vary from one batch of strips to the next and even from one strip to the next within a batch. Nevertheless, within a batch of strips manufactured altogether with the same starting components, this relationship can more or less be determined. Thus, in FIG. 5, we see a plot of current in microamps versus glucose concentration from a set of samples dosed with differing levels of glucose applied to several sensors from the same batch. Points 24 show the sensor measurements in microamps for known amounts of glucose within the samples.

The sensor measurements here represent the current developed at the working electrode within a certain time period say five or six seconds. Even within a batch there is a certain amount of variation, as shown by the spread of points in FIG. 5. A fit through the data such as line 26 therefore may have standard deviations associated with it such as line 26' or line 26". In determining the slope and intercept of the line 26, therefore, the slope "m" and intercept "c" will themselves be associated with respective standard deviations "$\Delta m$", "$\Delta c$". By using the slope and intercept from an average subset of sensors derived in a calibration procedure such as that demonstrated with reference to FIG. 5, an individual sensor can be calibrated if the slope and intercept are available to correct the measured current at the working electrode or the measurement result.

Thus, meters typically are provided with a calibration code consisting of or embodying the slope and intercept calibration information so that a current from a sensor can be corrected to provide corrected glucose results to a user of the meter and sensor.

Figure 6:
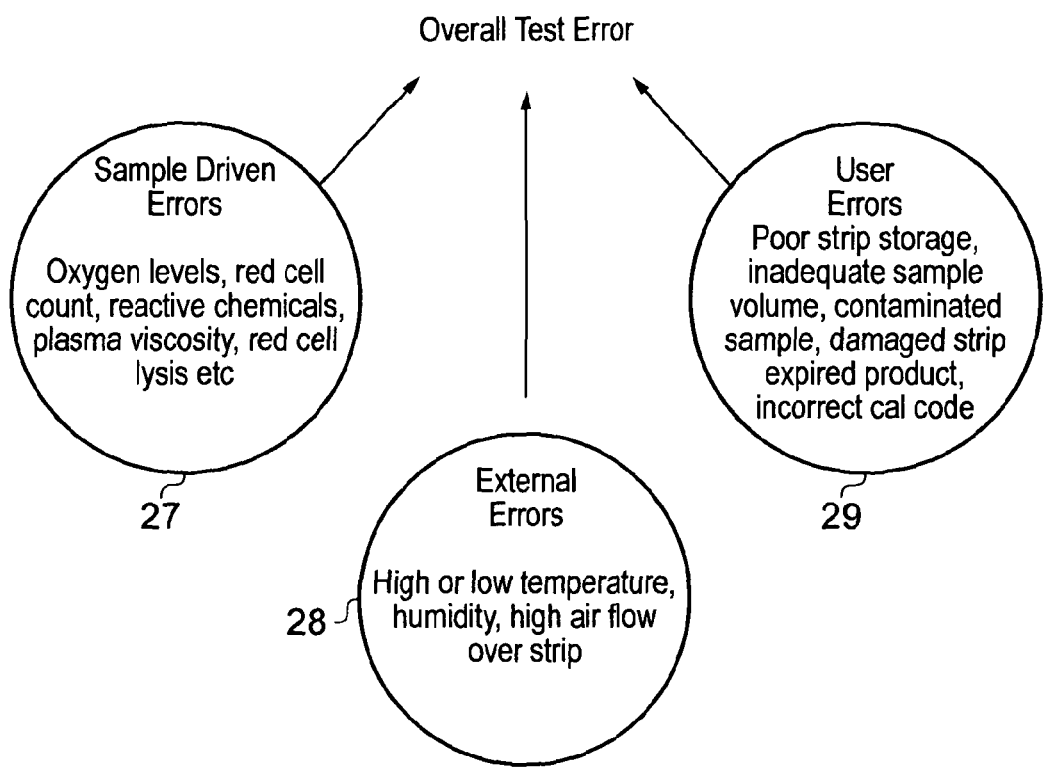
FIG. 6 is a schematic diagram showing the various contributions to the overall test error.

Thus, as can be seen in FIG. 6, the overall test error can be derived from a number of sources such as sample driven errors, external errors and user errors. Examples of sample driven errors 27 include oxygen levels, haematocrit, reactive chemical variation plasma viscosity, red-cell lysis and so on. Examples of external errors 28 include high or low temperature humidity high airflow over strip variations in humidity. Examples of user errors 29 include poor strip storage, inadequate sample volume, contaminated sample, damage strip, expired product, incorrect calibration code, and so on.

This invention seeks to address the influence of some of these errors when using test sensors.

FIG. 1 and FIG. 2 show two aspects of the invention. The first aspect of the invention is the provision of a dry reagent adjacent to dry calibration analyte. Here, this is achieved by locating a water-soluble dry reagent film 40 adjacent dried calibration analyte 38. Thus the reagent and the calibration analyte to which the reagent may be sensitive are located together in close proximity to one another. These may touch or lie within a few μm of one another but do not interact because these are in dry form. Thus the transport paths of the reaction products from the two sources of analyte to the measurement electrode are very similar. A preferred embodiment, also shown, is locating the dry reagent and calibration analyte also adjacent measurement electrode E2 to form a calibration electrode 19.

One component adjacent to another component means that the components, such as calibration analyte and reagent, may be located in physical contact or contiguous or juxtaposed or bordering or adjoining or abutting or overlapping or near one another. In one embodiment this may also mean that the calibration analyte and reagent may be so located without being attached and/or having any interaction therewith to any appreciable extent. In certain embodiments, for example, the reagent may be adjacent to the predetermined amount of first calibration analyte so that a wave front of fluid flowing along the flow path arrives at the reagent for the analyte of interest and at the first predetermined amount of a first calibration analyte at approximately the same time for example, within a time selected from the group of about 0.75 s, about 0.5 s, about 0.25 s, about 0.2 s, about 0.1 s, about 0.05 s, about 0.025 s, about 0.02 s, about 0.01 s. In certain embodiments, for example, the reagent may be adjacent to the predetermined amount of first calibration analyte to within a distance of the order of zero μm (when touching) or on the order of units or tens of μm, or within about 5 to 15 μm, or within about 10 μm, or within about 5 μm of one another.

When two wet compositions are located adjacent to one another, these almost inevitably mix due to the surface tension of the fluid within the compositions drawing the wet surfaces of the compositions together. Components within the compositions can mix and interact with one another until the liquid is removed by drying. The result is that one composition is attached to the other when these are dried.

When a wet composition is located adjacent a dry composition, assuming the dry composition is soluble and the surface of the dry composition is not hydrophobic, the dry composition will dissolve into the wet composition at its surface. Thus, components within the compositions can mix and interact with one another until the liquid is removed by drying. The result is that one composition is attached to the other.

When two dry compositions are located adjacent one another, there can be no mixing and therefore whilst the compositions are located adjacent to one another these are not attached to one another.

A dry composition is one that is sufficiently free from moisture or liquid, for example, so that its component molecules are not free to move with respect to one another.

The second aspect is the presence of calibration electrode having a predetermined amount of calibration analyte thereon upstream of a working electrode with respect to the fluid flow. A third aspect of the invention is a combination of the first two aspects. These and further aspects of the invention are described in more detail elsewhere.

The predetermined amount of calibration analyte may be known very precisely, known within certain limits or unknown. However, from one sensor to the next the predetermined amount of calibration analyte may be predetermined to be the same within specific tolerances whether or not the actual absolute quantity of analyte on a test sensor is known. Thus whilst the exact quantity of calibration analyte disposed, e.g. by ink jet printing, on respective sensors may not be known, the manufacturing process may be controlled enough to provided equivalent amounts on respective measurement electrodes in respective sensors.

Similarly, aspects of the present invention enable manufacture of reagent film suitable for the purpose of providing reagent film for test sensors so that in certain embodiments of the invention each sensor is provided with the same quantity of reagent within certain tolerances. In certain embodiments it is desirable for the reagent film to have a substantially even concentration of analyte per unit area so that providing an equivalent area of film to one or more measurement electrodes in one or more sensors results in each measurement electrode being provided with equivalent quantity of reagent although the quantity of reagent provided to each may not be known.

The tolerances required for the amount of calibration analyte derive from tolerances in reagent film production and tolerances in sensor construction. The tolerance values that may be desirable, or indeed in certain embodiments may be required are dictated by the sensor design such as one or more of the following: geometry of the flow path, height of the flowpath, width of the flowpath, length of the flowpath, location along the flowpath of at least the first calibration electrode, location along the flowpath of at least the first working electrode, distance between the first calibration electrode and the first working electrode, dissolution rate of the reagent, dissolution rate of the first predetermined amount of the first calibration analyte, thickness of the reagent, thickness of the reagent film.

Thus, the control of the predetermined amount of calibration analyte that is provided in each sensor and control of variation from sensor to sensor may be good but the actual quantity of calibration analyte provided in each may not be known. It is desirable that the variables in sensor design and manufacture are controlled to optimise the performance of the sensor. For example, such optimisation may include control of variables so that a suitable measurement indicative of the concentration of the analyte of interest can be taken at one working electrode before calibration analyte or reaction products from a calibration electrode can travel by diffusion or otherwise from the calibration electrode to the working electrode.

Any one or more aspects of the invention may use a web based production method. In particular a reagent film as described herein may be made by a web production method. Preferably, a reagent film may be used in a web production method to manufacture a sensor according to the invention. Examples of web based manufacturing techniques that may be used include those described in WO2001/73109 and WO2004/040290 (both INVERNESS MEDICAL; DAVIES et al)

Figure 7A:
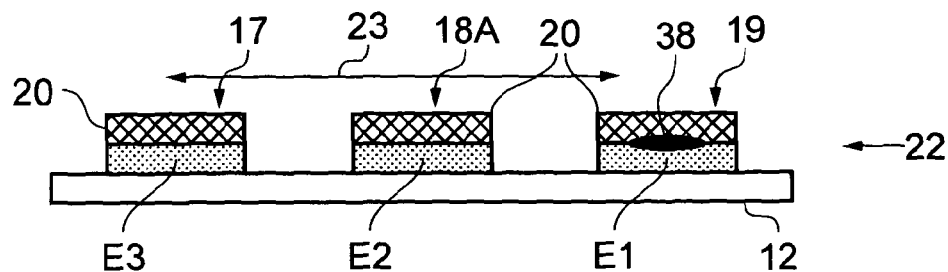
In FIG. 7A calibration electrode 19 lies upstream of working electrode 18A and counter/reference electrode 17.
Figure 7B:
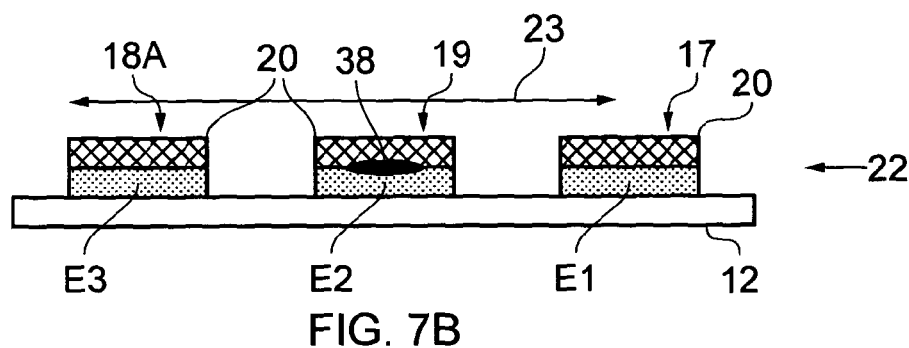
In FIG. 7B calibration electrode 19 lies upstream of working electrode 18A and downstream of counter/reference electrode 17.
Figure 7C:
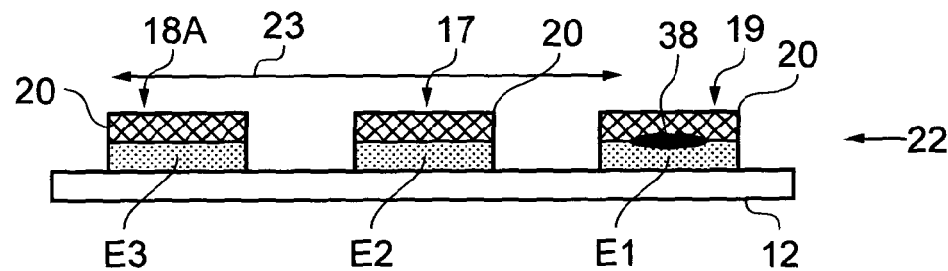
In FIG. 7C calibration electrode 19 lies upstream of counter/reference electrode 17 which itself lies upstream of working electrode 18A.

FIGS. 7A, 7B and 7C show in cross section, example embodiments of the invention according to the first and second aspects. A substrate 12 is provided with three measurement electrodes E1, E2, E3. The three Figures show cross sectional views of a test sensor such as that seen in FIGS. 1, 10A, 10B, 11, 13, 22A, 22B, 22C and 22D. Whilst the cross sections of the various components are here depicted as approximately rectangular or in the case of the predetermined amount of analyte 38 approximately planar or an amorphous dot, it will be understood by those skilled in the field that the cross-section may vary depending upon the deposition technique. Indeed, control of the exact cross sectional shape or indeed the exact thickness can be varied to optimise the performance of the devices.

Hereinafter, it will be understood that measurement electrodes E1, E2, E3 and so on will encounter fluid flowing through the device the sensor on the flow path in the direction from E1 to E2 to E3 to E4 and so on, unless otherwise specified. In FIGS. 7A, &B and 7C fluid flows from right-to-left in direction 22 along flow path 23. For the present purposes the exact dimensions particularly in cross section and or length of the flow path can be left to one side. Nevertheless, it should be understood that the dimensions of the flow path are important in determining the volume of fluid required (important for a body fluid sample such as blood or interstitial fluid) and for the rate of flow of fluid within the sample chamber. This can therefore have an effect on the timing of the reaction as will be discussed in more detail later.

In FIG. 7A, sample fluid encounters first measurement electrode E1, here a calibration electrode 19 comprising conductive measurement electrode E1 overlaid, at least in part, by a predetermined amount of calibration analyte 38 and a dry reagent film 20. Thus, the dry predetermined amount of calibration analyte 38 and the dry reagent film 20 are adjacent to one another and in this example embodiment overlaying one another at least in part and furthermore also adjacent to and overlaying at least in part measurement electrode E1.

Measurement electrode E2 is provided over at least part of its surface with dry reagent film 20. Thus, measurement electrode E2 and reagent film 20 form a working electrode 18A. Downstream of measurement electrode E2 is measurement electrode E3 which is also provided with a reagent film 20 and functions as a counter/reference electrode during a measurement.

In FIG. 7B measurement electrode E1 is exposed to the wave front flowing along flowpath 23 in direction 22 first. Next, calibration electrode 19 comprising measurement electrode E2, predetermined amount of calibration analyte 38 and reagent film 20 encounters the fluid wave front. Downstream of the calibration electrode 19 is working electrode 18A comprising measurement electrode E3 and reagent film 20.

In FIG. 7C, calibration electrode 19 is the first to encounter the fluid flowing along flowpath 23 in direction 22. Next, measurement electrode E2 encounters the fluid and thus forms counter/reference electrode 17 comprising measurement electrode E2 and reagent film 20. Downstream again is a working electrode 18A comprising measurement electrode E3 and reagent film 20.

The size and/or shapes of measurement electrode E1, E2, E3 and their respective layers can be varied as would be understood by one skilled in the art. Thus, it may be that the counter/reference electrode E2 is twice the size of a working electrode. The shape and/or area of the electrodes may be the same or may be different. If one or both of these are the same, this can reduce the likely source of error in comparing the current from one electrode to that of another. Or the current developed at one electrode can be multiplied by the ratio of the areas to adjust for any difference in areas. Typically, a conductive electrode layer 13 (see FIG. 1) forming measurement electrode E1, E2, E3 is laid down at one time, and therefore these have the same thickness on substrate 12.

In one embodiment, all the measurement electrodes E1, E2 and E3 serving as working and/or calibration electrodes are of the same size and shape, so as to create similar reaction and diffusion conditions near each. Furthermore, the construction, size and shape of electrodes may be controlled. This is because it is desirable to reduce variations from one electrode to the next, particularly between calibration electrodes and working electrodes, and optionally between calibration electrodes where more than one is provided.

It is not necessary for the reagent and the calibration analyte in dry form to be free from water in any state in other words to be anhydrous but rather that they are sufficiently free from liquid or moisture that there can be no transport of active ingredients therebetween. This enables analyte in the form of calibration analyte to be placed very close to reagent so that any reaction occurring between the calibration analyte and the reagent or between the reagent and sample analyte commences at approximately the same time. By same time it is meant within a sufficiently short time period such that the measurement of current developed at the calibration electrode at a specific time point say at five or six seconds is not subject to variation due to the differing start times of the reactions between the calibration analyte and the reagent and between the sample analyte sample and the reagent. For a sensor having a measurement time period for a current developed at an electrode of between 4 and 12 seconds or about 5 or about 10 seconds, the difference in the start time of the reaction between the calibration analyte and reagent and the sample analyte and reagent is preferably less than 0.5 seconds, 0.25 seconds, 0.2 seconds, 0.1 second, 0.05 seconds, 0.025 seconds, 0.02 seconds, 0.01 second.

Furthermore, it can be seen that because of the location of the calibration analyte and the reagent layer immediately adjacent to, in this example embodiment, the uppermost exposed layer of the measurement electrode, the reaction products from the two sources of analyte have a very short and indeed approximately the same distance to travel to develop a current at the measurement electrode.

Figure 8:
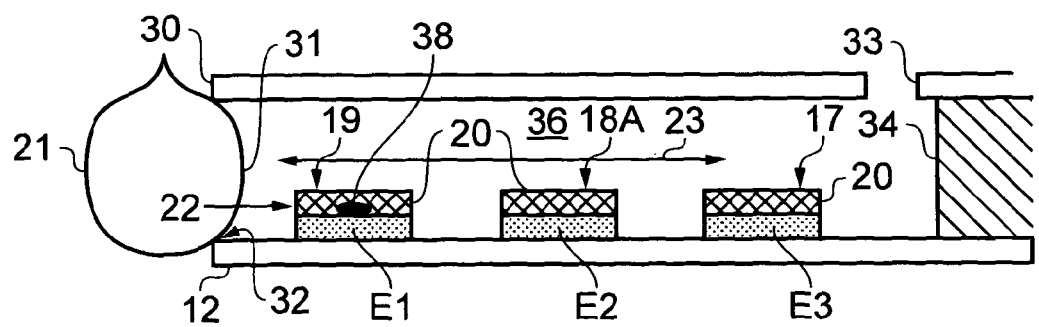
FIG. 8 shows cross sectional view of an exemplary embodiment of a test sensor according to the invention.

One example of fluid transport is shown in FIG. 8 in which a fluid drop 21 is placed very close to fluid entrance 32 such that wave front 31 of drop 21 engages with at least one surface of chamber 36 so as to be drawn along flow path 23 by capillary action.

Here substrate 12 is provided with three measurement electrodes E1, E2 and E3. Measurement electrode E1 provides a calibration electrode by the provision of a predetermined amount of dried calibration analyte 38, in this case glucose and a dry reagent film 20. Measurement electrode E2 provides the working electrode 18A and measurement electrode E3 provide a counter reference electrode 17. A spacer 34 provides a gap between substrate 12 and a sample chamber lid 30. Sample chamber lid 30 is provided with an air vent 33 that functions as a capillary fluid stop and allows air to vent from the sample chamber 36. The spacer 34 and sample chamber 36 are sized and shaped to provide a capillary channel along which fluid can flow in direction 22. Thus, chamber 36 provides a flow path 23 from fluid entrance 32 to air vent 33. Wave front 31 of blood drop 21 engages first with calibration electrode 19 then with working electrode 18A and then with counter reference electrode 17. Because of the close proximity of the calibration analyte 38 with the reagent film 20, as the fluid passes containing analyte of interest, all the ingredients for the reaction dissolve and are able to interact together. As will be shown later, the rate of dissolution of the reagent layer formed by reagent film 20 may be dependent upon its thickness (see FIG. 21). Chamber 36 provides a capillary channel for drawing fluid along flow path 23 by capillary action.

As can be seen in FIG. 8, the calibration analyte 38 and the reagent film 20 are located adjacent to one another on one side of the chamber 36, thus on one side with respect to the bulk of the fluid sample which would flow along the flowpath 23. Similarly, calibration analyte 38 and reagent film 20 and in this embodiment, measurement electrode are located on one side of chamber 36, thus one side with respect to the bulk of the fluid sample which would flow along the flowpath 23. Further, the calibration analyte 38 and the reagent film 20 lie between the flowpath, (and hence the bulk of the fluid when fluid is present) and the measurement electrode E1. This is a particularly desirable arrangement.

Figure 9A:
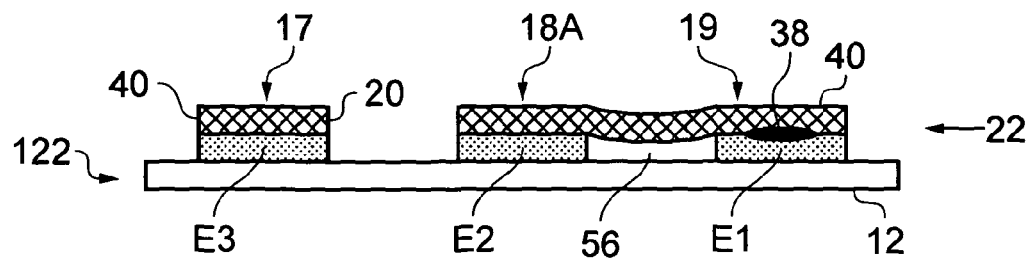
FIG. 9A shows a cross sectional view of an exemplary embodiment a test sensor according to the invention.
Figure 9B:
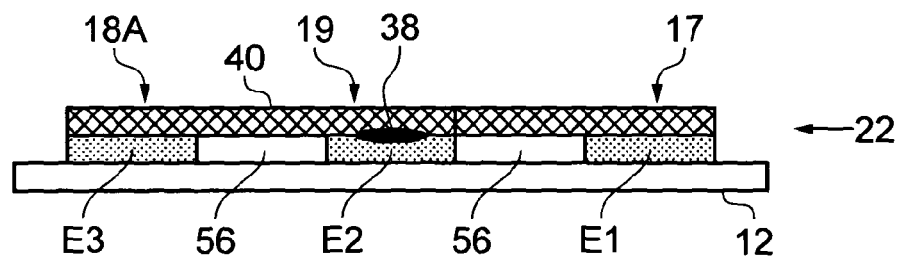
FIG. 9B shows a cross sectional view of an exemplary embodiment of a test sensor according to the invention.
Figure 9C:
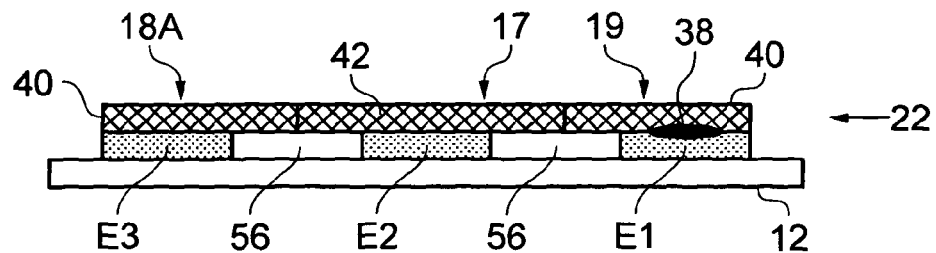
FIG. 9C shows a cross-sectional view of an exemplary embodiment of a test sensor of according to the invention.

Turning now to FIGS. 9A, 9B and 9C an alternative embodiment of the invention is shown in which the reagent layer is provided in the form of a dry film having a greater lateral dimension extending over two or three measurement electrodes. In this example embodiment, the reagent was in the form of a dry film having two exposed, opposing, generally parallel planar surfaces prior to construction of the sensor. Thus, the film could be said to form a reagent layer when it is overlaid onto another surface so that at least one of its exposed surfaces remains exposed.

In FIG. 7A, 7B, 7C and FIG. 8, the calibration electrode lies upstream of the working electrode. This enables flexibility in the design of the electrode placement and the sensor as a whole to meet the needs of fast measurement times and small sample volume. Where more than one calibration electrode and/or more than one working electrode are provided it is sufficient that at least one of the calibration electrodes lies upstream in terms of fluid flow of at least one of the working electrodes according to the second aspect of the invention.

In combination with the first aspect of the invention, namely the provision of dry reagent adjacent to dry calibration analyte, the timing of the measurement in a sensor according to this aspect of the invention is designed to be such that the reaction products from the reaction at the upstream i.e. calibration electrode do not have time to drift or defuse downstream to the working electrode. This means that the current developed at the working electrode is reflective of the sample analyte concentration immediately adjacent the working electrode and not the sample and calibration analyte concentration which is immediately adjacent the calibration electrode. There is indeed more flexibility in designing the sensor if the restriction on where to place the calibration electrode upstream of the measurement electrode were not present. Nevertheless, by constructing an electrode that functions appropriately with no cross talk between measurement signals from upstream and downstream electrode signals, a sensor having the small sample volume and fast test times at least as good as those used at present yet with greater accuracy in measurement result due to improved on-strip calibration, can be developed.

In FIGS. 9A, 9B and 9C reagent layer is provided in the form of a water-soluble dry reagent film 20, 40. In FIG. 9A, one part of the dry reagent film forms dry reagent film 20 of similar size and shape to measurement electrode E3.

Dry reagent film 40 has been pre-formed and placed upon substrate 12 after formation of measurement electrodes E1, E2 and E3 and placement of calibration analyte 38 thereupon. Dry reagent film 40 has an extended lateral size of the order of the distance between neighbouring measurement electrodes, say around a few millimeters or between about 0.5 to about 5 mm. There may be a gap 56 between measurement electrodes such as E1 and E2 underneath reagent film 40. Reagent film 40 covers three measurement electrodes in the embodiments shown in FIGS. 9B and 9C.

It is within the scope of the invention that the reagents film 40 covers 1 or 2 or 3 or 4 or more measurement electrodes to form working electrodes and/or counter/reference electrodes and/or calibration electrodes. It is also within the scope of this invention that the reagent film 40 is provided in parts so, for example, a first film covering a first set of one or more measurement electrodes and a second film covering a second set of one or more measurement electrodes. Alternatively, or in addition, the reagent film may be provided in parts so that the parts overlay one another thus reagent film 40 may be supplemented by a second reagent film overlaying it. Reagent film 20, 40 may be square rectangular, oval, circular and may have one or more apertures provided through it which may also be square, rectangular, oval or circular or any other suitable shape. For example, a background electrode having no reagent thereon may be provided by a reagent film having an aperture therethough overlaying a measurement electrode in the region of the aperture.

In this example embodiment in FIG. 9A, fluid flows in direction 22 encountering measurement electrode E1 in the form of calibration electrode 19 first followed by working electrode 18A followed by counter/reference electrode 17. An alternative embodiment may be provided in which the geometry of the sensor may be arranged so that fluid flows in direction 122.

In FIG. 9B measurement electrode E1 provides a counter/reference electrode 17 upstream of a calibration electrode 19 which is itself upstream of a working electrode 18A. Here reagent film 40 covers completely three electrodes located within the sensor namely measurement electrodes E1, E2 and E3.

In FIG. 9C, an alternative design of reagent film 40 is shown in a counter/reference electrode 17 is located between calibration and working electrodes. Measurement electrode E1 is also provided with a predetermined dose of calibration analyte 38. Reagent film 40 is a dry reagent film. In this case, this means sufficiently free from liquid or moisture and, in one preferred embodiment, free from water so that the film can be placed next to the calibration analyte without any appreciable interaction therebetween. Thus the reagent film 40 can be placed adjacent to the calibration analyte 38.

In one preferred embodiment of the invention, the reagent, for example in the form of reagent film 40, is pre-formed. This may mean pre-forming the reagent prior to the formation of sensor 10. Alternatively this may mean during the construction of sensor 10 so a dry reagent is formed before it is added to sensor 10. This is so that during construction of sensor 10, the reagent and the calibration analyte are brought together to be adjacent to one another when in dry form. In one embodiment when a reagent film is provided it is desirable for reagent film 40 to be sufficiently strong, for example sufficiently thick, to be handled separately during manufacture. Nevertheless, it is also desirable that reagent film 40 is sufficiently thin so as to dissolve rapidly within the time frame of the measurement.

In example embodiments, whilst it may be that calibration analyte 38 covers all of an exposed surface of a measurement electrode, such as measurement electrode E1, this need not necessarily be the case. Likewise, whilst reagent film 20 or extended dry reagent film 40 may cover all of a measurement electrode and/or all of a calibration analyte 38, this need not necessarily be the case.

Figure 10A:
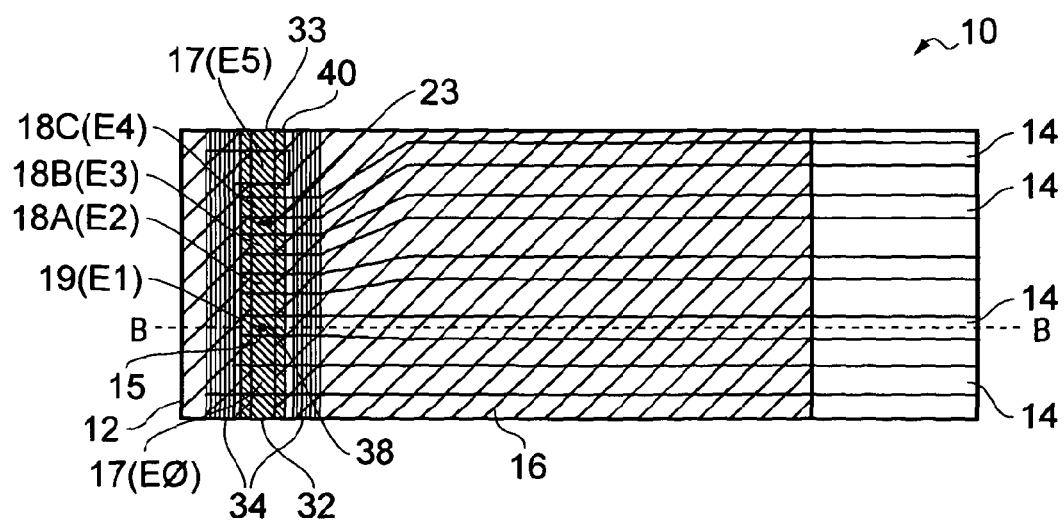
FIG. 10A shows a plan view of an exemplary embodiment of test sensor having five measurement electrodes according to one or more aspects of the invention.
Figure 10B:
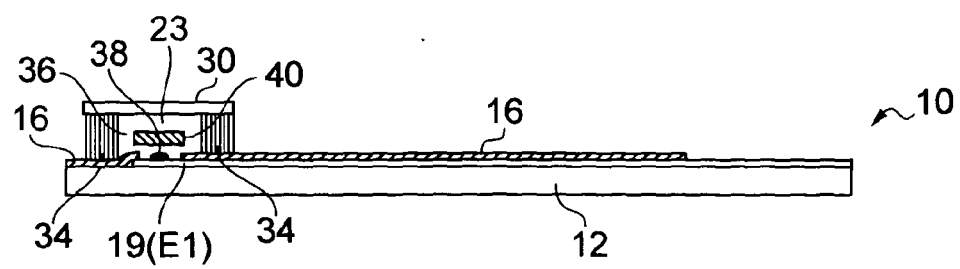
FIG. 10B shows a cross-sectional view along line BB' of the test sensor of FIG. 10A.

FIG. 10A shows a plan view of a sensor 10 having a conductive layer 13 (not labelled) comprising conductive tracks 14 and measurement electrodes E0, E1 E2 E3 and E4 and E5 located thereon. An insulation layer 16 defines an insulation window 15 which in turn defines the widths of the measurement electrodes E0, E1, E2 etc. FIG. 10B shows a side cross-sectional view of sensor 10 along line BB'. Spacer 34 supports a chamber lid 30 and together these provide a sample chamber 36. Sample chamber 36 is sized and/or shaped and/or constructed (for example by provision of a hydrophilic surface) to provide fill of the sensor by capillary action. For example, sample chamber 36 may provide a single linear capillary channel defining a flowpath 23 extending from fluid entrance 32 to air vent 33. Thus, a flow path 23 is provided between fluid entrance 32 and air vent 33. Measurement electrodes E0 and E5 are formed from the same conductive track and provide a counter/reference measurement electrode. A predetermined amount of calibration analyte, for example glucose, 38 is provided on measurement electrode E1 to form along with overlaying reagent film 40, calibration electrode 19. Reagent film 40 is a water-soluble dry film. The water-soluble dry reagent film 40 extends from measurement electrode E0 to measurement electrode E5 and indeed all the way to the elongate edge of sensor 10 and substrate 12 thereof. The portions of water-soluble reagent dry film 40 overlying one or more of measurement electrodes E2, E3 or E4 may be deactivated by processes known to those skilled in the art for example heat or radiation to inactive the reagent thereon and provide a background electrode similar in construction to the working electrodes. Alternatively, a background electrode may be provided with no reagent film associated with it. Thus a reagent film may be provided of a size and/or shape which does not overlay a measurement electrode so that a background electrode can be provided.

Similarly, in one embodiment, measurement electrodes E2, E3, E4 may have an identical buffer solution deposited thereon, except that one of these is not provided with calibration analyte in the buffer solution, so as to form a working electrode of similar construction to a neighbouring calibration electrode without the calibration analyte.

Thus, it is possible to make background and/or calibration and/or working electrodes as nearly identical to one another as possible in construction so as to reduce variations in measurements from these electrodes caused by variations in their separate construction.

Dry film means sufficiently free from liquid or moisture, for example water, such that the components of the film are held fixedly in place with respect to one another and with respect to the outermost surfaces of the film. This means that the film components cannot interact with any other active ingredients adjacent to the film, for example, calibration analyte 38 on calibration electrode 19.

Measurement electrodes E2, E3 and E4 are also overlaid with water-soluble dry reagent film 40 to form working electrodes 18A, 18B and 18C. Thus, during measurements three sample analyte currents derived from these three working electrodes can be gathered and if appropriate averaged or otherwise combined to provide an estimated sample analyte current. This can result in reduced error in the sample analyte current.

The length of each measurement electrode in the same direction as the direction of flow path 23 is defined by the width of conductive tracks 16 in the region of the measurement electrodes E0, E1, E2 etc. The width of the measurement electrodes in the direction substantially perpendicular to the direction of flow path 23 is defined by the insulation window of insulation layer 16. It will be appreciated by those skilled in the art that the dimensions and/or shape of the measurement electrodes can be varied by varying the insulation window width and/or shape, and/or the width and/or shape of the conductive tracks.

Figure 11:
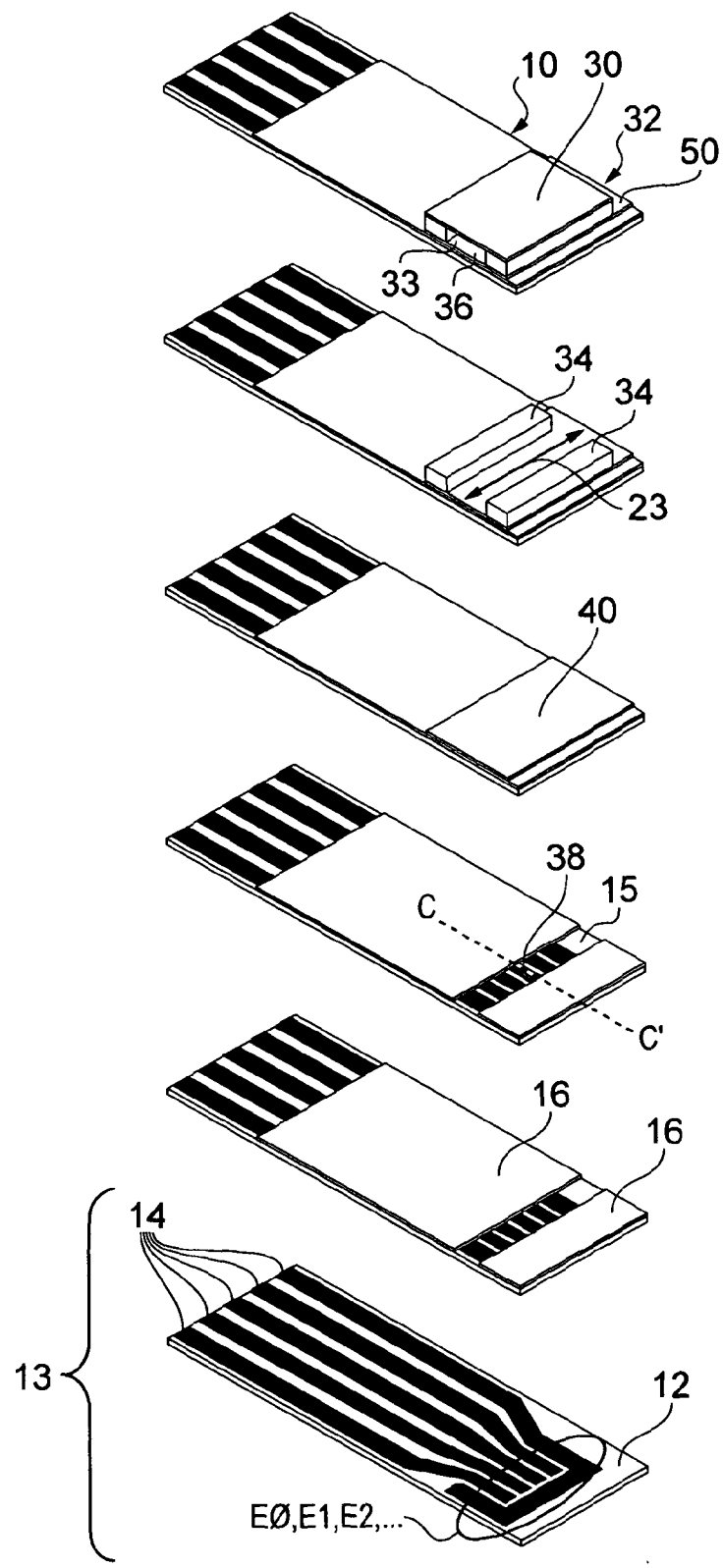
FIG. 11 shows a perspective view of an exemplary embodiment of a test sensor at various stages of manufacture according to one or more aspects of the invention.

FIG. 11 shows sensor 10 at several stages of construction. Firstly, a substrate 12 is provided with a conductive layer 13 comprising electrode tracks 14 and measurement electrodes E0, E1, E2 etc. Substrate 12 may be any suitable material known to those skilled in the art such as plastic, polythene. Conductive tracks 14 may comprise the same material as measurement electrodes E0, E1, E2 although this need not necessarily be the case. These may be deposited by a technique known to those skilled in the art such as sputtering, screen printing, lithographic techniques, rotagravure printing. Next, an insulation layer 16 is deposited in appropriate registration over electrode tracks 14. Typically insulation layer 16 is fixed by pressure adhesive to substrate 12. Next, a predetermined amount of calibration analyte 38 is deposited on one of the measurement electrodes defined by insulation window 15 of insulation layer 16. Next, optionally, a mask is used to enable deposition of a pressure adhesive pattern on insulation layer 16 as will be seen in connection with FIG. 12. This pressure adhesive is optionally, provided to enable a pre-formed water-soluble dry reagent layer 40 to be placed fixedly on the insulation layer. Other method of fixing can be envisaged and are covered by this invention.

Chamber 36 provides a capillary channel defining a flow path for drawing fluid along it by capillary action. The reagent layer may be in the form of a dry film having, prior to the construction of the sensor device two exposed, opposing and generally parallel planar surfaces. Dry reagent film 40 is placed upon insulation layer 16 of sensor 10; it becomes a layer having one exposed, generally planar surface. Typically, the water-soluble dry film is dissolvable in water, plasma, blood, urine, saliva or other aqueous liquid, preferably substantially dissolvable or more preferably substantially completely dissolvable. Chamber walls 34 in the form of spacer 34 are provided to define chamber 36 and flow path 23 from fluid entrance 32 to air vent 33. A chamber lid 30 may also be provided atop spacer 34. As can be seen in the uppermost picture of sensor 10 in FIG. 11, spacer 34 and chamber lid 30 are somewhat shorter than the width of substrate 10 reagent layer film 40 and insulation layer 16. Thus, a shelf 50 is provided, optionally, in the region of one of the long edges of sensor 10.

Figure 12:
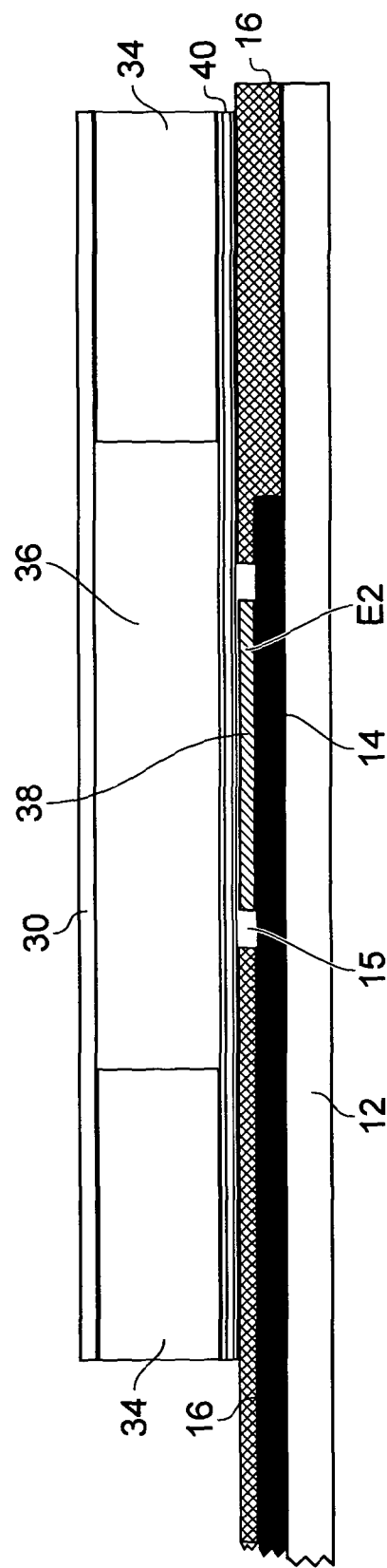
FIG. 12 shows a cross-sectional view of the test sensor of FIG. 11 along line CC'.

FIG. 12 shows a cross-section through lines C-C' of the sensor of FIG. 11. Here substrate 12 is provided with insulation layer 16 defining insulation window 15. A predetermined amount of calibration analyte 38 is provided on the exposed surface of conductive tracks 14 in the form of measurement electrode E2. Spacer 34 is topped by chamber lid 30 providing sample chamber 36 for fluid to pass through. Water-soluble dry reagent film 40 lies on top of insulation layer 16 and calibration analyte 38.

Water soluble dry reagent film 40 comprises, in one example embodiment, a first film forming ingredients, such as polymer, and a first active ingredient sensitive to the analyte of interest. It may also comprise a second film forming ingredient. Either first and/or second film forming ingredient, where this is provided, may be formed from one or more of the following: a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose. Typically, a combination of film forming ingredients are provided, one having better dissolution and less hydrophilic properties, the other having less good dissolution and more hydrophobic properties. In this way, the relative strengths and dissolution properties of the dry reagent film 40 can be controlled. As will be discussed elsewhere herein the dissolution rates and structural strength of the water-soluble dry reagent film can be important in ensuring good robust manufacturing whilst at the same time providing good dissolution of the film and any reactive ingredients therein to provide an analyte signal within an appropriate timeframe.

Thus, the wavefront arrives at both the calibration analyte and the dry reagent adjacent to it at more or less the same time. Thus, the wavefront arrives at these components within a time selected from the group of 0.75 s, 0.5 seconds, 0.25 seconds, 0.2 seconds, 0.1 second, 0.05 seconds, 0.025 seconds, 0.02 seconds, and 0.01 seconds.

Furthermore, in one example embodiment the wavefront arrives at the calibration analyte and the dry reagent adjacent to it and at the measurement electrode adjacent to these at more or less the same time. Thus, the wavefront arrives at these components within a time selected from the group of 0.75 s, 0.5 seconds, 0.25 seconds, 0.2 seconds, 0.1 second, 0.05 seconds, 0.025 seconds, 0.02 seconds, and 0.01 seconds.

Therefore, by appropriate selection of the ingredients and of the water-soluble dry reagent film and of the calibration analyte, and by locating these in dry form in close proximity adjacent to one another various functions are provided for. Firstly, there is no appreciable reaction between the calibration analyte and the active ingredient(s) within the reagent, until fluid arrives and dissolves these components. Secondly, because these are in close proximity, the wavefront arrives at same time and the interaction of these components can begin immediately more or less. Thirdly because these are located adjacent to the measurement electrode, the transport paths of the reaction products from these two sources are very similar lengths and current from these two reactions can develop more or less at the same time.

Figure 13:
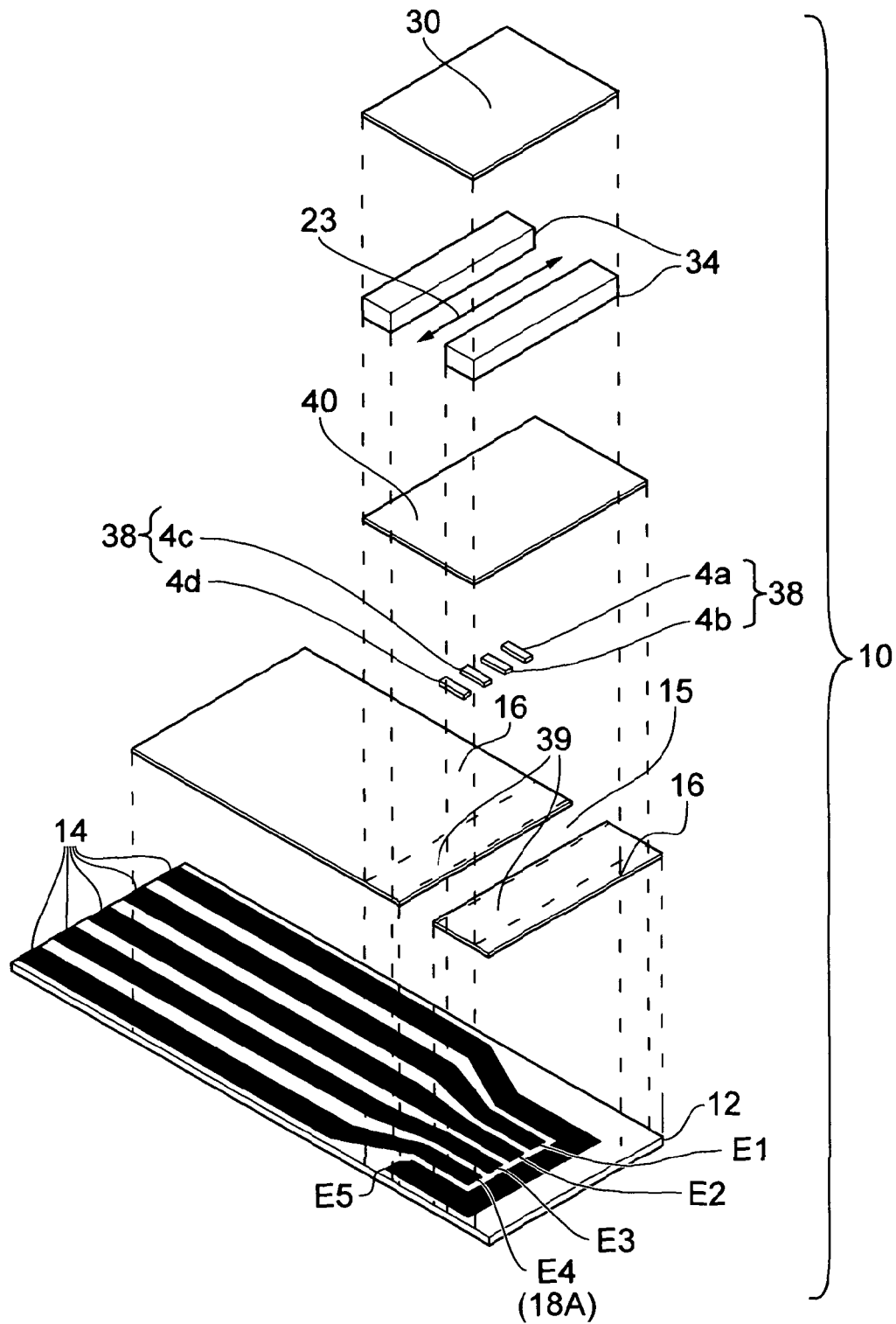
FIG. 13 shows an exploded perspective view of another exemplary embodiment of a test sensor according to one or more aspects of the invention.

FIG. 13 shows a perspective exploded view of an alternative embodiment of the sensor according to the invention. A pattern of adhesive 39 is shown overlaid on insulation layer 16. In contrast with the embodiments shown in FIGS. 10, 11 and 12, this example sensor 10 is provided with three predetermined amounts of calibration analyte. These are 4a 4b and 4c. 4d is a predetermined amount of base, such as a buffer, identical to that used in the preparation of the predetermined amount of calibration analyte. For example, calibration analyte may be prepared using a buffer having an analyte such as glucose. A similar amount of buffer, without any analyte, is provided in 4*d* on measurement electrode E4. Thus, measurement electrode E4 now forms, along with reagent film 40, a working electrode 18A.

In more detail now, in FIG. 13, one embodiment of the invention is shown in which the analyte test strip comprises a planar substrate 12. The substrate 12 may be made of any suitable material such as polyester. Conductive tracks 14 are disposed on the substrate 12 such that one end of the substrate forms a suitable connection into the meter and the other end is formed into multiple measurement electrodes E1, E2, E3 etc. The tracks may be disposed on the substrate by screen printing a suitable carbon graphite paste. It is important to control the exposed area of conductive material and other methods of creating electrodes with good control of the exposed area may be envisioned. Alternative conductive materials may be used such as gold or palladium which may be coated onto the substrate surface and cut into the desired electrode patterns with an excimer laser or may be coated through a mask to form the desired pattern. An insulation layer 16 is disposed over the conductive tracks such that sufficient track is exposed at one end of the strip to form electrical contact when the strip is inserted into a strip port connector of a meter (not shown) and a defined area of each track is exposed at the other end of the strip to form multiple measurement electrodes E1, E2, E3 and E4.

To form the internal standard a controlled quantity of a glucose solution 4*a*, 4*b*, 4*c*, is then dosed onto one or more of E1, E2 and E3. The glucose dosing solution may also contain 1% Blanose 7LF and a surfactant such as Zonyl® FSN-100 (DuPont). The dosing of the glucose solution may be done through known deposition techniques such as ink-jet printing or drop-on-demand technologies. The glucose dose is then dried at ambient temperature or by using an oven or forced air dryer. The amount of glucose dosed onto one or more of the detection areas may be the same or different from the other dosed areas. 'Blank' solutions 4*d* containing Blanose and surfactant but no glucose may also be dosed onto the detection areas that are not dosed with glucose.

One of the detection areas may also be turned into a background measurement electrode by either deactivating the enzyme in the film over this area or by not placing reagent film over this particular area or removing the reagent film over this area.

The ferricyanide in this example may also be included in the glucose dosing solution and deposited on the measurement electrodes along with the standard glucose dose.

Other optional polymers suitable for use in making the reagent containing film are modified starch, pullulan, hydroxyethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates.

Figure 14:
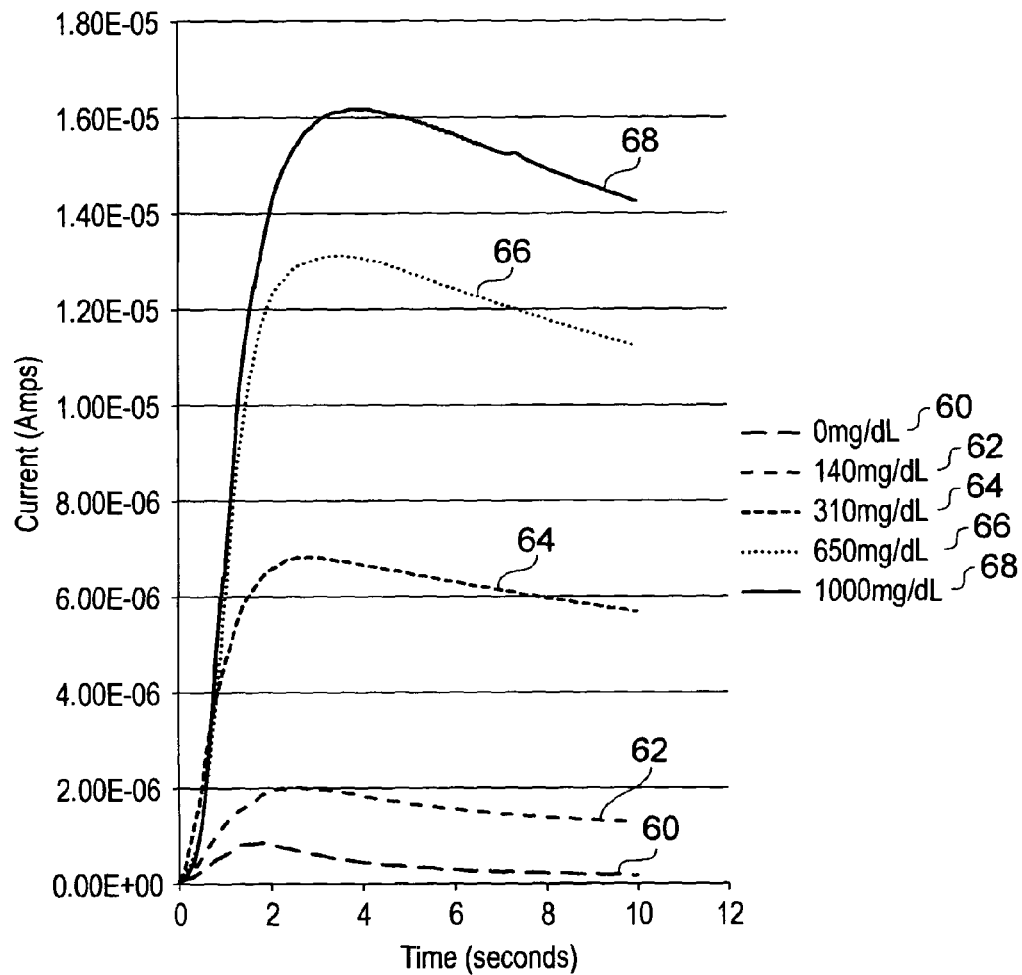
FIG. 14 shows plots of experimental data, namely, current measured against time at a single detection area for various levels of glucose in a sample comprising buffer for a test sensor constructed according an exemplary embodiment of one or more aspects of the invention wherein a water-soluble dry reagent layer is pre-formed prior to placement in the sensor. No calibration analyte is dosed onto a measurement electrode.

Additional optional components may also be included in the reagent film, such as:
  plasticizers e.g. xylitol, sorbitol, erythritol, polyethylene glycol
  disintegrants e.g. microcrystalline cellulose, sodium croscarmellose or sodium starch glycolate
  surfactants e.g. fluorosurfactants such as ZONYL® FSN-100 or a silicone polyether copolymer such as Dow Corning® 193C FIG. 14 shows a plot of currents measured at a single detection area with no additional dose of glucose on the detection area surface. Plots are shown at various levels of glucose in a buffer sample.

FIG. 14 shows data, in particular currents measured at a single detection area against time i.e. current developed at a single working measurement electrode with no additional dose of glucose over time. Glucose was used as the sample analyte in a suitable buffer. Variation of current level with sample glucose can be seen. Curve 60 shows current measurement when no glucose was present in the sample. Curve 62 shows current measurement when 140 mg per deciliter concentration was in the sample. Curve 64 shows the current developed for a glucose concentration of 310 mg per deciliter. Curves 66 and 68 show respectively currents developed for glucose concentrations of 650 mg per deciliter and 1000 mg per deciliter.

Figure 15:
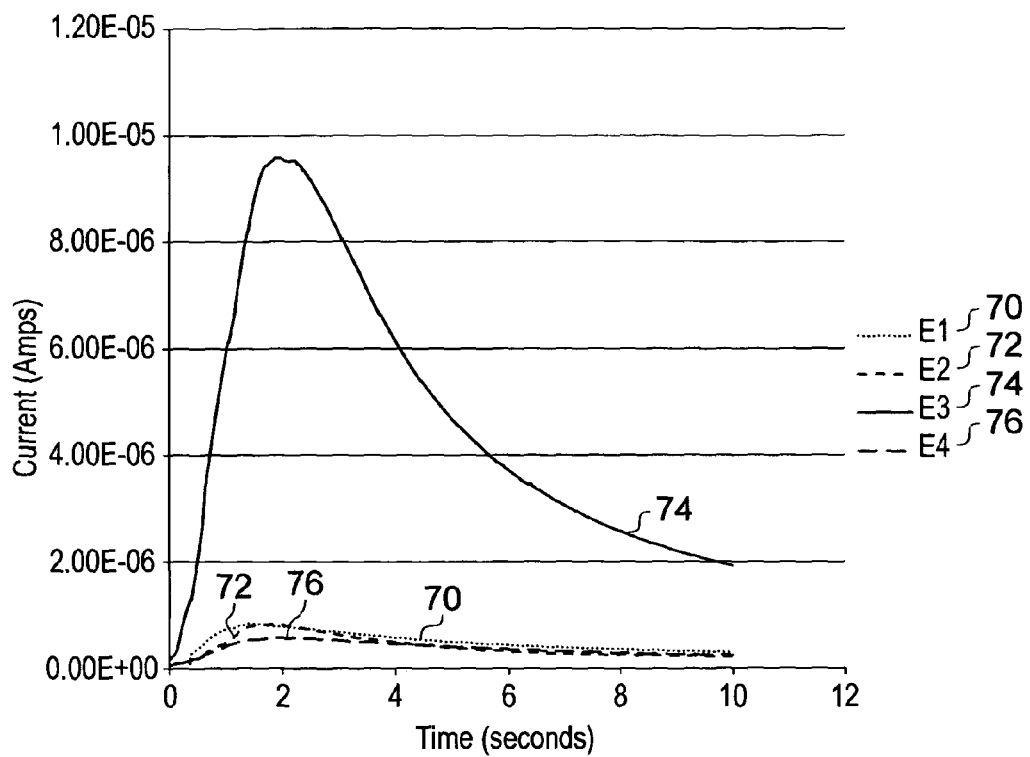
FIG. 15 shows plots of experimental data, namely, current measured against time at four different detection areas i.e. measurement electrodes E1, E2, E3, and E4. One of the measurement electrodes E3 has a dose of glucose inkjet printed onto it and dried prior to sensor assembly.

FIG. 15 shows a plot of current measured at different detection areas (E1-E4). E3 has a dose of glucose ink-jet printed on it and dried prior to strip assembly. The sample solution was buffer containing no glucose. FIG. 15 shows a plot of current measured on different detection areas measurement electrodes E1, E2, E3 and E4 using a sensor such as that shown in FIG. 11. E3 has had a predetermined amount of glucose inkjet-printed onto it and dried prior to sensor assembly. The sample solution used for the test was buffer and contained no glucose, therefore no sample analyte. As expected, the current developed at measurement electrodes E1 and E2 shown in curves 70 and 72 was very low since the glucose dose on measurement electrode E3 was downstream of these two measurement electrodes. The current developed at measurement electrode E3 shows the presence of glucose on that electrode. Somewhat surprisingly, the current developed at measurement electrode E4 shows no glucose has reached this electrode within the timeframe of the assay as shown in curve 76. This is unexpected as working measurement electrode E4 is downstream of the measurement electrode E3 dosed with glucose and functioning as a calibration electrode. Thus, these results demonstrate that the geometry of the flow path, the location of the calibration electrode, the location of a downstream working electrode, the dosed glucose analyte, the spacing of the measurement electrodes E3 and E4 and so on can be selected so that had a fluid sample with sample analyte been used, a suitable measurement indicative of the concentration of the sample analyte could be completed at the working electrode (E4) before fluid containing calibration analyte or associated reaction products could travel from the calibration electrode (E3) to the working electrode E4.

Once the capillary channel is filled, the transfer of reaction products from the calibration electrode E3 to the working electrode E4 is dependent upon the dissolution of the starting ingredients and diffusion of the reaction products and/or the reaction starting ingredients. Thus, the assay time for a measurement to be taken is less than the time taken for diffusion of calibration analyte or reaction products to any other measurement electrode.

Figure 16:
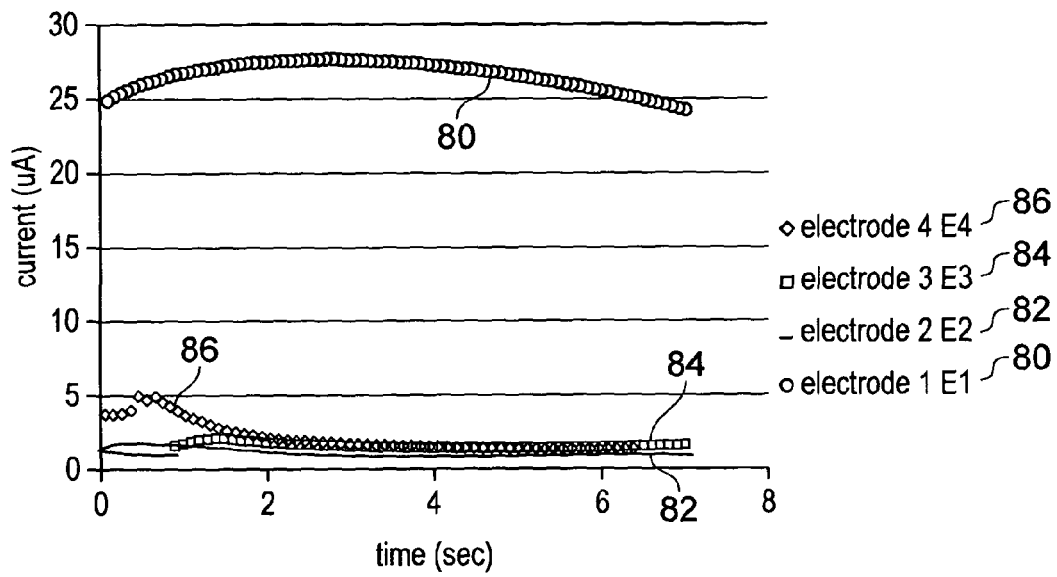
FIG. 16 shows plots of experimental data of current against time in an early prototype four measurement electrode system in which one measurement electrode. In this case E1 is pre-dosed with a predetermined amount of glucose and a water-soluble dry reagent film was pre-formed prior to construction of the sensor.

FIG. 16 shows plot of current against time for a similar experiment in which the first electrode in the flow path E1 is provided with a dose of glucose as calibration analyte. Curve 80 shows the presence of glucose on this measurement electrode. However, downstream electrodes E2, E3 and E4, as shown by measurement curves 82, 84 and 86, show no contamination of analyte detected at these electrodes within the timeframe of the assay.

Figure 17:
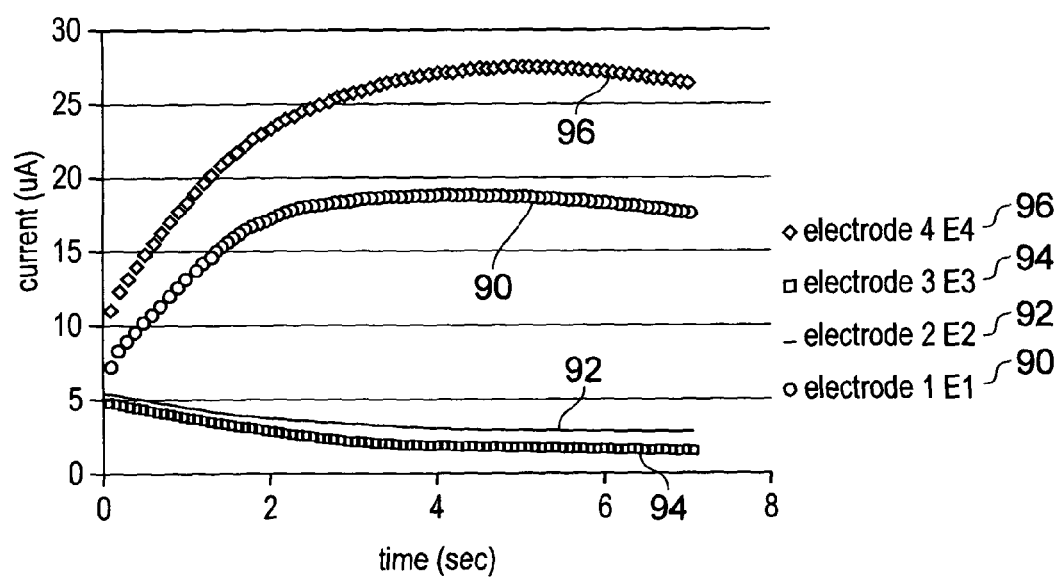
FIG. 17 shows plots of experimental data of current against time for a four electrode system in an exemplary embodiment of test sensor according to the invention in which E1 and E4 are both provided with a predetermined amount of glucose.

FIG. 17 shows a plot of real data of current against time in some early prototype test sensors. Here, electrode E1 has a certain dose of calibration analyte, for example, glucose. This can be seen in curve 90. Electrode 4 has a different dose of calibration analyte thereon. This is demonstrated by a current measurement seen in curve 96. Intermediate electrodes along the flow path E2 and E3 show no glucose present thereon as no significant current has been measured. Thus, there is no crosstalk from electrode E1, as demonstrated by curve 90, to electrodes E2 and E3 as seen in curves 92 and 94, nor indeed to electrode E4, since there is no sudden increase or other change in this curve.

FIG. 18A shows a plot showing the current at 10 seconds as measured on a detection area with no dosed glucose (E4) and a detection area with additional dosed glucose (E3) at three different levels of control solution. FIG. 18A shows current developed at a measurement electrode at a measurement time of 10 seconds against glucose concentration for the same detected area with no dosed glucose (E4) and a detection area with additional dosed glucose (E3) at three different levels of control solution (buffer with different levels of glucose to provide different glucose concentrations). Thus, in this experiment test sensors were each provided with an equivalent dose of glucose as calibration analyte on their respective electrodes E3. Three samples of control solution were used as fluid samples and currents were measured at measurement electrodes E3 or E4 in each of the sensors. Graph 100 shows the relation between current and glucose concentration at calibration electrode E3 using control solution of differing glucose concentrations. Graph 102 shows the relation with current versus glucose concentration for working electrode E4 again using control solution of differing glucose concentrations.

The current developed at working electrode E4 is less than that developed at calibration electrode E3 which has been provided with additional dosed glucose. This shows that the additional glucose provided on the calibration electrode E3 provides a constant step change in magnitude of the current at different glucose concentrations in the sensors, demonstrating that the sensors are responding in a similar way to the same amount of glucose calibration analyte. This constant step change is equivalent to $S \cdot i_s$ where $i_s$ is the calibration current and S is a slope correction factor.

FIG. 18B shows plots of experimental data of current developed at particular working electrodes (E3 with additional dosed glucose and E4 with no dosed glucose) at 10 seconds versus glucose concentration in milligrams per deciliter using whole fingerstick blood (2 repetitions at each glucose level). The standard dose of calibration glucose used here was greater than that used in the experiment in connection with FIG. 18A. FIG. 18B shows that the additional calibration glucose provided on the calibration electrode E3 provides a constant step change in magnitude of the current at different glucose concentrations in blood in the sensors, demonstrating that the sensors are responding in a similar way to the same amount of glucose calibration analyte. The difference in intercept at zero glucose concentration between the lines fitted by least squares fitting to the data points give a good estimate of $S \cdot i_s$.

Internal Standard Correction of Glucose Measurement

If we consider a measurement system with 3 current measurement electrodes where:

Calibration measurement electrode E1 has a predetermined amount of glucose dosed on it and therefore measures the total calibration current due to glucose in the sample+the predetermined calibration dose;

Working measurement electrode E2 measures total working electrode current due to glucose in the sample;

Background measurement electrode E3 has no enzyme and therefore only measures non-glucose dependent current i.e. current due to interferents and other noise effects.

The measured currents at the calibration measurement electrode E1 and the working measurement electrode E2 are the sum of the glucose dependent current and a non-glucose dependent intercept or background current. Therefore the currents measured on each electrode can be described as:

$$E1\ \text{response} = i_m + i_s + i_b$$

$$E2\ \text{response} = i_m + i_b$$

$$E3\ \text{response} = i_b$$

Where $i_m$=current from sample glucose=error free working electrode current. (We can assume this current is substantially identical in E1 and E2, if these are of the same area and have been constructed to same design and by the same method.)

$i_s$=current from internal standard calibration dose $i_b$=non-glucose background current.

However due to interferents, sample haematocrit, test conditions etc there are also error contributions to all these currents. Errors in the background response are additive whereas errors in the glucose dependent current are multiplicative. That is the background error will be a specific current irrespective of the glucose level but the glucose dependent error will be a percentage of the glucose current (both sample and internal standard). Therefore actual currents measured will have error contributions at each electrode as follows:

$$\text{actual } E1\ \text{response } i_c = S \cdot i_m + S \cdot i_s + (i_b + I)$$

$$\text{actual } E2\ \text{response } i_w = S \cdot i_m + (i_b + I)$$

$$\text{actual } E3\ \text{response} = i_b + I$$

Where S is the slope error factor and I is the intercept error current, $i_c$ is the measured calibration electrode current and $i_w$ is the measured working electrode current.

Both $i_s$ and $i_b$ have known expected values under 'normal' conditions.

The intent of the internal standard is to allow the determination of S so that an error free working electrode current $i_m$ due to sample glucose can be derived and used to return an accurate sample glucose measurement.

Therefore given the three measured current responses from E1, E2 and E3 the background response measured at E3 can be subtracted from both the E1 and E2 response. Then subtracting the background corrected E2 (E2c) response from the background corrected E1 (E1c) response gives the current generated by the internal standard multiplied by the slope error factor ($S \cdot i_s$).

In fact just subtracting E2 from E1 gives the same value as the background current is eliminated in this subtraction. The value of E2c is needed later. Thus $$E1 - E2 = E1c - E2c = S \cdot i_s$$

As $i_s$ has a known expected value, for example, determined from another sensor or subset of a batch of sensors as described with reference to FIGS. 19A, 19B and 19C, we can determine the value of S.

$$S = (E1 - E2)/i_s = (E1c - E2c)/i_s \qquad \text{Equation 1}$$

Using the now determined value of S we can derive the correct value of $i_m$ from the background corrected response of E2.

$$E2c = E2 - E3 = S \cdot i_m$$

Therefore, $$i_m = i_s(E2-E3)/(E1c-E2c) \qquad \text{Equation 2}$$

Alternatively if no background electrode is present or background is assumed to be negligible within the framework of the test, than we can derive the correct value of $i_m$ from the response of E2 (therefore $i_m = i_s(E2)/(E1-E2)$)

The value of error free working electrode current $i_m$ is then used to return an error corrected glucose value, for example by using a calibration graph 26 in FIG. 5, or by using the values of m and c, from such a fit through such a graph, or by using a code indicative of a value of m and c.

An example of determination of error free working measurement electrode current is shown in EXAMPLE 4.

Figure 19A:
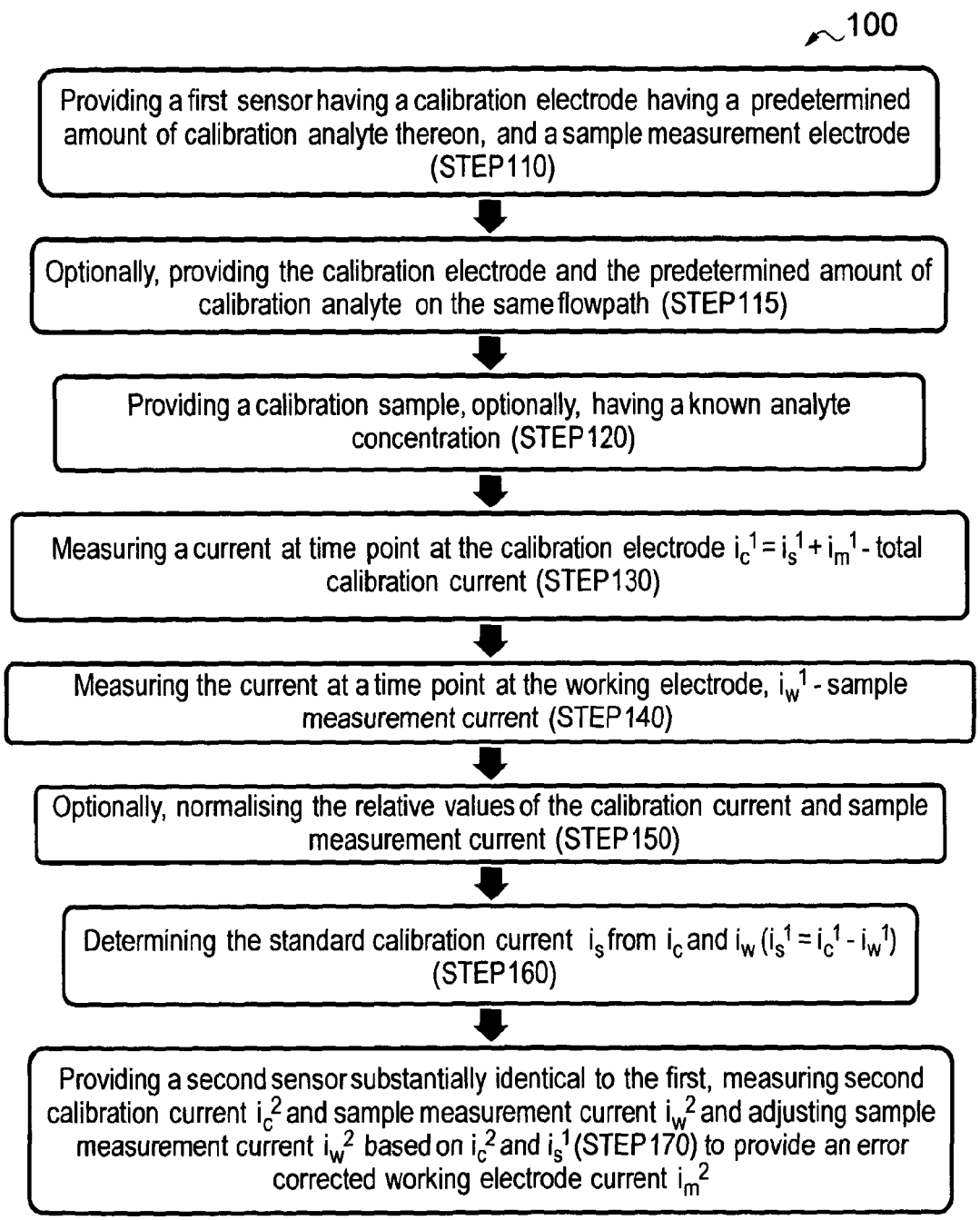
FIG. 19A shows a method of correcting the current at a working electrode to provide a corrected glucose result using the calibration current developed at a calibration electrode having a predetermined amount of glucose thereon as part of the correction factor.

FIG. 19A shows a method 100 of calibrating a sensor according to one aspect of the present invention. Step 110 is providing a first sensor (sensor 1) having a calibration electrode having a predetermined amount of calibration analyte thereon and a sample measurement electrode. Optionally the calibration electrode and the predetermined amount of calibration analyte are on the same flow path (Step 115). Step 120 is providing a calibration sample optionally having a known analyte concentration. Step 130 is measuring the current, optionally at a time point or at an endpoint or steady-state at the calibration electrode $i_c^1 = i_s^1 + i_m^1$ (total calibration current of sensor 1). Step 140 is measuring the current developed at the sample measurement electrode at a time point or at an endpoint or steady-state. Step 150 is optionally, normalising the relative values of the calibration current and sample measurement current to take account of different electrode areas. Step 160 is determining the standard calibration current $i_s$ from $i_c$, and $i_m$, thus $i_s^1 = i_c^1 - i_m^1$.

Step 170 is providing a second sensor (sensor 2) preferably identical within manufacturing tolerances to the first. Step 170 also includes measuring current developed at a corresponding working electrode at a corresponding time point on the second sensor, $I_c^2$ and $I_m^2$ (and the calibration current developed at the corresponding calibration electrode) and adjusting $i_m^2$ based on $i_c^2$ and $i_s^1$.

Figure 19B:
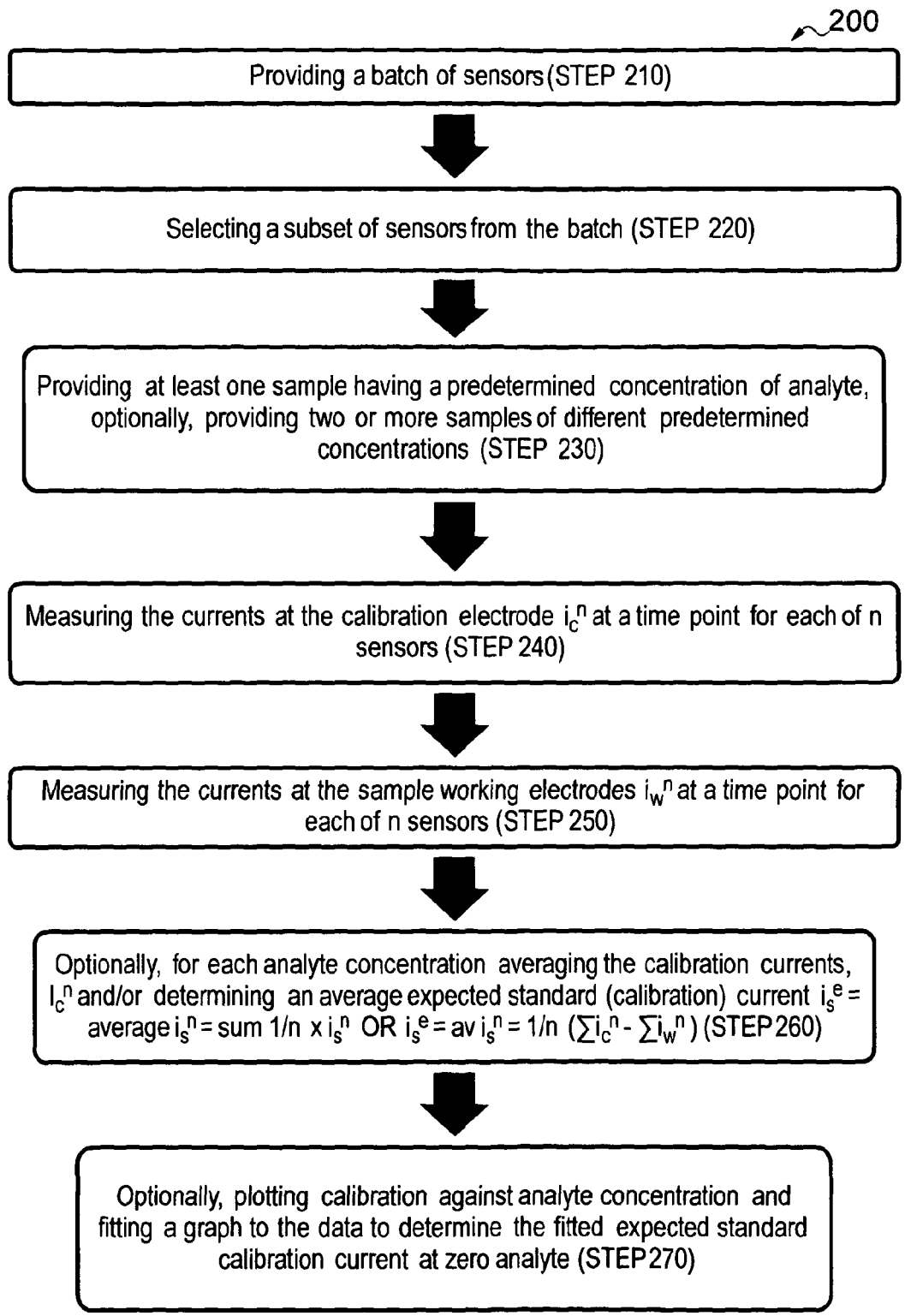
FIG. 19B shows a method of determining expected standard calibration current for a batch of sensors for use in correcting an individual sensor measurement.

FIG. 19B provides a method of calibrating a batch of sensors according to a further aspect of the present invention. Method 200 comprises a first step 210 of providing a batch of sensors. Step 220 comprises selecting a subset of sensors from the batch. Step 230 comprises providing at least one sample having a predetermined concentration of analyte, optionally providing two one more samples of different predetermined concentrations of analyte. Step 240 comprises measuring the currents at the calibration electrodes $i_c^n$ at a time point. Optionally the time point is a specific time point when the reaction has settled down enough to provide current measurements correlated to the total sample and calibration analyte concentration or the time point may be as the reaction goes to completion or towards steady-state.

Step 250 comprises measuring working electrode currents $i_m^n$ at the sample measurement electrodes at a time point in n sensors or at n electrodes in one or more sensors. Optionally the time point may be a specific time point during which the reaction has settled down enough for there to be a correlation between analyte concentration and the current developed at the working electrode or it may be as a reaction goes to endpoint or to a steady-state.

Optionally a step 260 is provided comprising, for each analyte concentration, averaging the calibration currents, $i_s^n$ and/or the actual measured calibration currents $i_c^n$ and working electrode currents $i_w^n$ and summing these over n sensors to determine an average expected standard calibration current from $$i_s^e = av\, i_s^n = 1/n(\Sigma i_c^n - \Sigma i_w^n).$$

Optionally an alternative step 270 is provided comprising plotting the calibration current for one or more sensors at two or more values of the analyte concentration and fitting a graph to the data to determine the fitted expected standard calibration current at zero analyte.

FIG. 19C shows a plot of current at a calibration electrode in microamps against analyte concentration in milligrams per deciliter for a subset of sensors selected from a batch of sensors at three different levels of analyte concentration 310, 320 and 330. Graph 335 is fitted to the data 310, 320, 330 and is extrapolated back to the Y axis to give the expected standard current at zero analyte concentration. This is in effect the current expected from the presence of calibration analyte on the calibration electrode in a predetermined amount ($i_s^e$) when no sample analyte is present.

FIG. 19D shows three further optional steps for methods 100 or 200. Step 350 comprises repeating for each calibration electrode in a sensor (if more than one calibration electrode). Step 360 comprises using the determined expected standard current $i_s^e$ and measured calibration current to adjust the sample measurement current from a further sensor to provide a corrected sample measurement current.

Figure 20:
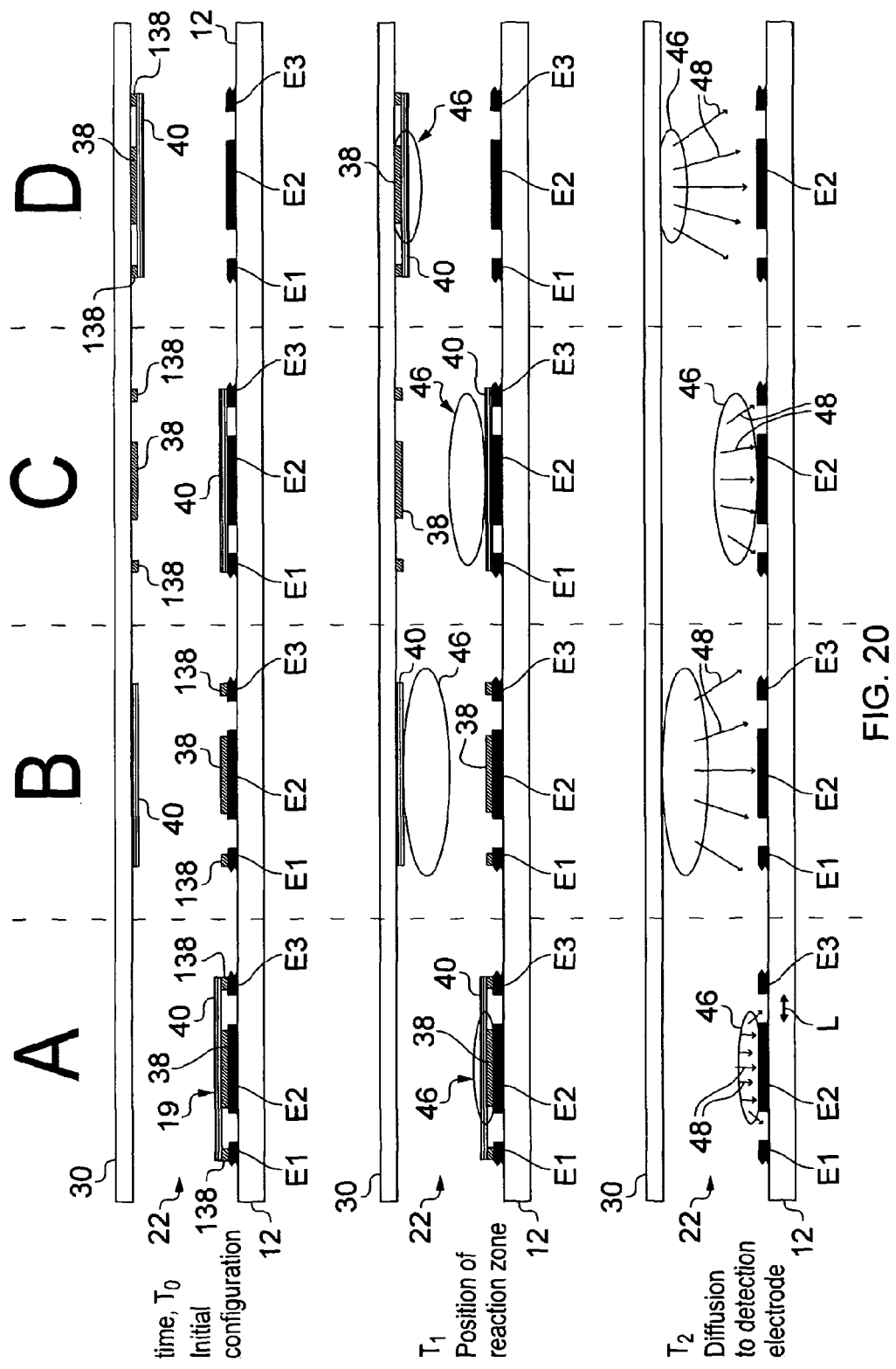
FIG. 20 shows four example structures A, B, C and D at three different times, T0, T1 and T2 to illustrate the location of the reaction zone upon introduction of fluid along the flow path and the likely diffusion of reaction products to the measurement electrodes.

Referring now to FIG. 20, four different strip design configurations are shown:

A Detection electrode, reagent film and standard dose adjacent to one another on one side of the sample chamber B Standard glucose dose on the detection electrode and reagent film on other side of sample chamber C Reagent film next to detection electrode and standard glucose dose on other side of sample chamber D Reagent film and standard glucose dose on opposite side of sample chamber to detection electrode This Figure illustrates the importance of keeping the reagents, standard glucose dose and detection electrode in close proximity on achieving short assay times and low sample volumes. When the sample enters the strip the reagents and glucose dose are solubilised and start to diffuse into the sample. Glucose and ferricyanide diffuse at similar rates and an order of magnitude faster than the enzyme glucose oxidase. Therefore in the early seconds of the assay the enzyme reaction largely takes place close to where the enzyme was positioned in the sample chamber. The main reaction zone 46 is shown in the above Figure for each assay configuration. The products of the reaction 48 then need to be detected at the surface of the detection electrode. If these reaction products have further to travel they will also spread further in the sample chamber and the different detection electrodes will need to be spaced further apart to avoid "cross talk" between electrodes. Alternatively the detection electrodes may be physically separated in separate sample chambers. Either option adds sample volume and/or complexity to the test strip.

A short assay time minimises the distances travelled by the assay reagents and requires the reagents to be initially placed in close proximity to each other and the detection electrode. Only configuration A achieves this but novel strip designs are required to prevent any reaction occurring during strip manufacture.

Thus, FIG. 20 shows four structural arrangements for a sensor A, B, C and D at three different time points T0, T1 and T2. The sensors are shown in cross-section through a calibration electrode. Sensor A comprises a calibration electrode 19 in accordance with one aspect of the present invention. Here calibration analyte 38 is adjacent reagent film 40 and both are adjacent measurement electrode E1 on the same side of the sample chamber with respect to the fluid sample. A substrate 12 is provided with three neighbouring measurement electrodes E1, E2 and E3. A predetermined amount of calibration analyte here the same analyte as the analyte of interest is provided at 38. A water-soluble dry reagent film 40 is provided spanning measurement electrodes E1, E2 and E3. Only part of measurement electrodes E1 and E3 are shown nevertheless it can be seen that these measurement electrodes are also each provided with a predetermined amount of calibration analyte 138. Water-soluble dry reagent film 40 overlays the predetermined amount of calibration analyte on measurement electrode E1, E2 and E3. As has been described elsewhere, calibration analyte 38, 138 may be positioned in close proximity to water-soluble dry reagent layer 40 in any one of a number of ways not just the way displayed in configuration A. A chamber lid 30 is also shown.

Configuration B differs somewhat from configuration A. Here the water-soluble dry reagent layer 40 is not adjacent to the calibration analyte 38, 138. Configuration C shows a water-soluble dry reagent layer 40 overlaid measurement electrode E1, E2 and E3. Calibration analyte 38, 138 has been laid down on the lowermost surface of the chamber lid some distance away. Thus the water soluble dry reagent film 40 is again not adjacent to the calibration analyte 38, 138. Thus, neither configuration B nor C have reagent in the form of dry reagent film 40 in close proximity to calibration analyte 38, 138.

In configuration D, both calibration analytes 38, 138, and water-soluble dry reagent film 40 are co-located on the underneath of the chamber lid 30. Thus, reagent 40 is in close proximity with calibration analyte 38, 138 and therefore configuration D is one example embodiment of one aspect of the invention. Nevertheless, as these are remote from the measurement electrodes E1, E2 and E3, this embodiment is not optimal.

The initial configuration at time T0 in configurations A B C and D is shown with fluid approaching in direction 22. At time T1, the wavefront of fluid has passed from left to right and a reaction zone in which the water-soluble dry reagent film 40 and calibration analyte 38, 138 are dissolved or beginning to dissolve in the fluid to form a reaction zone 46 is shown. The reaction zone in configuration B is immediately adjacent the reagent layer 401.e near the chamber lid 3. This is because whilst calibration analyte 38 can dissolve in the fluid no reaction can take place until the reagent dissolving and diffusing into the reaction zone 46 reaches the calibration analyte 38 and ultimately the measurement electrode E2.

Turning now to configuration A, a reaction zone 46 is formed following passage of the fluid wavefront as dry reagent film 40 begins to dissolve in the fluid adjacent the measurement electrode E2. Furthermore, calibration analyte 38 also begins to dissolve in the fluid more or less at the same time and contributes to the analyte detected within the reaction zone 46. Calibration analyte, which in this case is the same as the analyte of interest, dissolves into the sample in the region of the reaction zone 46 and contributes along with sample analyte to the signal developed at adjacent measurement electrode E2. In configuration A, as can be seen at time T2, reaction products 48 have a very short distance to travel to measurement electrode E2 to develop a measurement current. The reaction products from the reaction with calibration analyte and from the reaction with sample analyte are very close to the measurement electrode E2 since the reagents film 40 and the calibration analyte 38 are located adjacent to one another and adjacent to the measurement electrode E2.

This is not the case in configuration B. In configuration B in more detail now, a reaction zone 46 is formed adjacent chamber lid 30 next to reagent film 40 as reagent film 40 dissolves into the sample fluid. Also, calibration analyte 38 will dissolve in reaction fluid in in close proximity to measurement electrode E2. For calibration analyte to contribute to current reagent and calibration analyte shall have to diffuse to the same location. Further, reaction products 48 from have to travel from the upper region of the chamber near the reagent layer to the measurement electrode E2 before a current can be measured at the measurement electrode E2. Indeed, it is thought that calibration analyte 38 needs to dissolve upwardly towards the region 46 in which reagent has been dissolved before calibration analyte 38 can react with reagent. Thus, the system requires more time before all the contributions to the variability of the system settle down. Thus, the system is not predisposed towards measurement at a time point shortly after commencement of the reaction.

In configuration C, at time T1, a reaction zone is formed adjacent the reagent layer as the reagent from the reagent film dissolves into the sample fluid and interact with the analyte of interest therein. This is located immediately above measurement electrode E2. However, the calibration analyte is located in the upper portion of the chamber and therefore it will take some time for the calibration analyte to dissolve and reach the reaction zone for reaction with the reagent. Thus, at time T2 the contribution of reaction products to the current developed at measurement electrode E2 is predominantly that from the sample fluid and not that from the calibration analyte. This results in a far more dynamic varying system in which the current developed at the measurement electrode E2 is not reflective of a combination of calibration analyte and sample analyte concentrations but rather is initially dependent upon sample analyte concentration and later is dependent upon calibration analyte concentration once this has defused to the region of the reaction zone immediately above the measurement electrode E2. In configuration D, this is not the case since the calibration analyte and sample analyte are collocated.

Furthermore in configuration D the calibration analyte and reagents film 40 are co-located on the roof of chamber 30. Here, a reaction zone 46 having contributions from the calibration analyte and the sample analyte concentrations is formed together. However, this reaction zone 46 is located towards the roof of the chamber. Thus, reaction products 48 at time T2 have to defuse towards the measurement electrode E2 before a current can be developed. Thus the start time of the reaction is different from the start time of the current developed at the measurement electrode E2. This is less than optimal.

Figure 21:
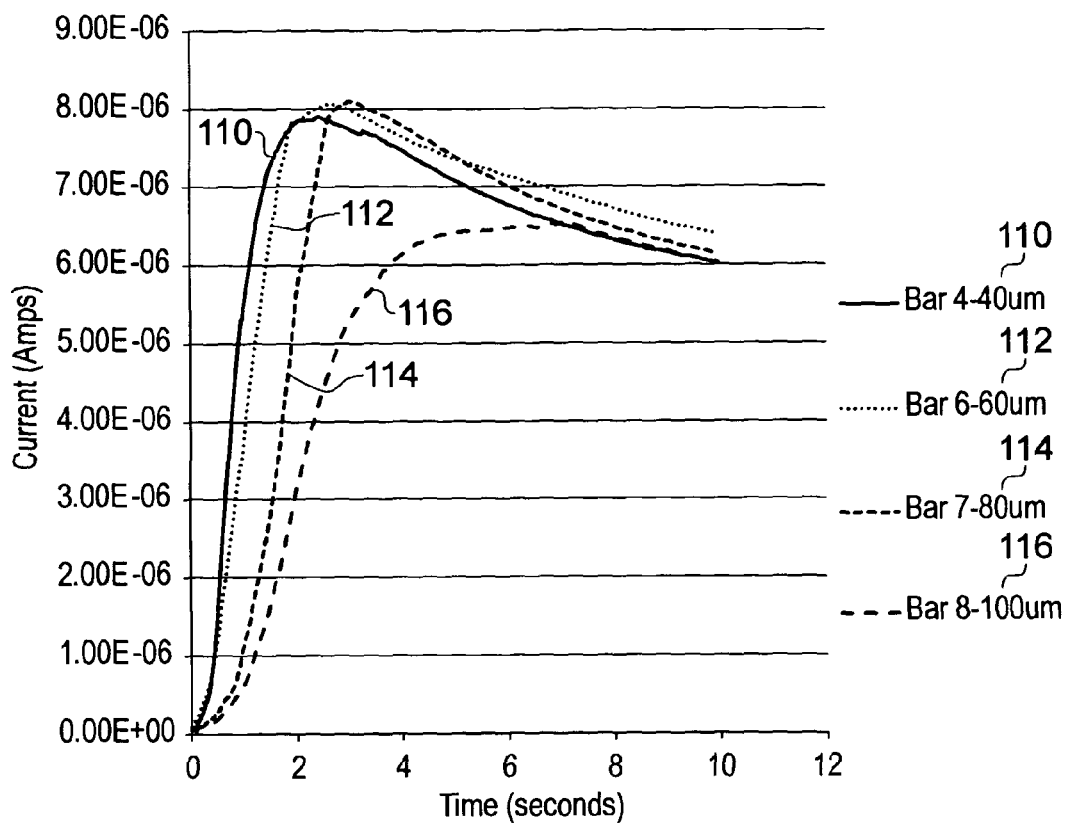
FIG. 21 shows a plot of experimental data of current versus time measured at the same respective measurement electrode in different sensors, each sensor having a water-soluble dry reagent film of differing dry thicknesses (based on their thicknesses when wet which were determined during manufacture).

FIG. 21 shows a plot showing the effect of film thickness on the dissolution rate of the active reagents as illustrated by the steepness of the rise in current in the first second of the assay. The sample was buffer with 310 mg/dL glucose. The film thicknesses shown are wet film thickness. FIG. 21 shows current against time for the same corresponding electrode in 4 different sensors using a variety of reagent film thicknesses. The selection of assay time, say 5 seconds, places constraints on the film thickness that may be suitable. Therefore, a thick film 100 µm 116 has a lower peak and slower rise and greater variation for longer than thicknesses of 80 µm 60 µm and 40 µm shown by curves 114, 112 and 110. Preferred thicknesses of water-soluble dry reagent film have a wet film thickness of about 90, 90 µm or less, about 80 or about 80 µm or less, or about 60 µm, or about 60 µm or less or between 40 and 90 µm, or between 40 and 80 µm. It is desirable for the film thickness to be sufficient to give the film strength for handling during manufacturing both of the film itself and of the sensor. Therefore, one might select the thickest film of the selection available thus one might select a film of wet film thickness 80 µm. However, the inventor has appreciated that an even thinner film may have appropriate handling strength and yet still carry enough reagent per unit area and therefore in a preferred exemplary embodiment, a film of wet thickness of 60 µm is used. This film shows a sufficiently rapid dissolution and reduction in variation of current by about 5-6 seconds to enable a measurement to be made.

A reagent film maybe produced by using a hand operated or automatic bar coater as known in the art. A wire bound bar coater may be used such as the K hand coater available from RK Print Instruments Ltd (Royston, Herts, UK). The bar number in FIG. 21 refers to the arbitrary value ascribed by the manufacturers of the bar coater to a thickness of wire bound around the bar which results in a wet film thickness of a particular dimension.

The dissolution rate of the film is important to the correct functioning of the test strip. The dissolution is in part a function of film composition and also of film thickness. FIG. 21 shows the effect of the film thickness on transient shape at 310 mg/dL glucose in buffer. The thinner the film the steeper the rise is in initial current and the earlier the current peaks. Thinner films will therefore allow shorter total assay times although if the film is too thin it becomes too fragile to handle and the lower amount of reagent present may start to limit the strip response at high glucose levels.

Figure 22:
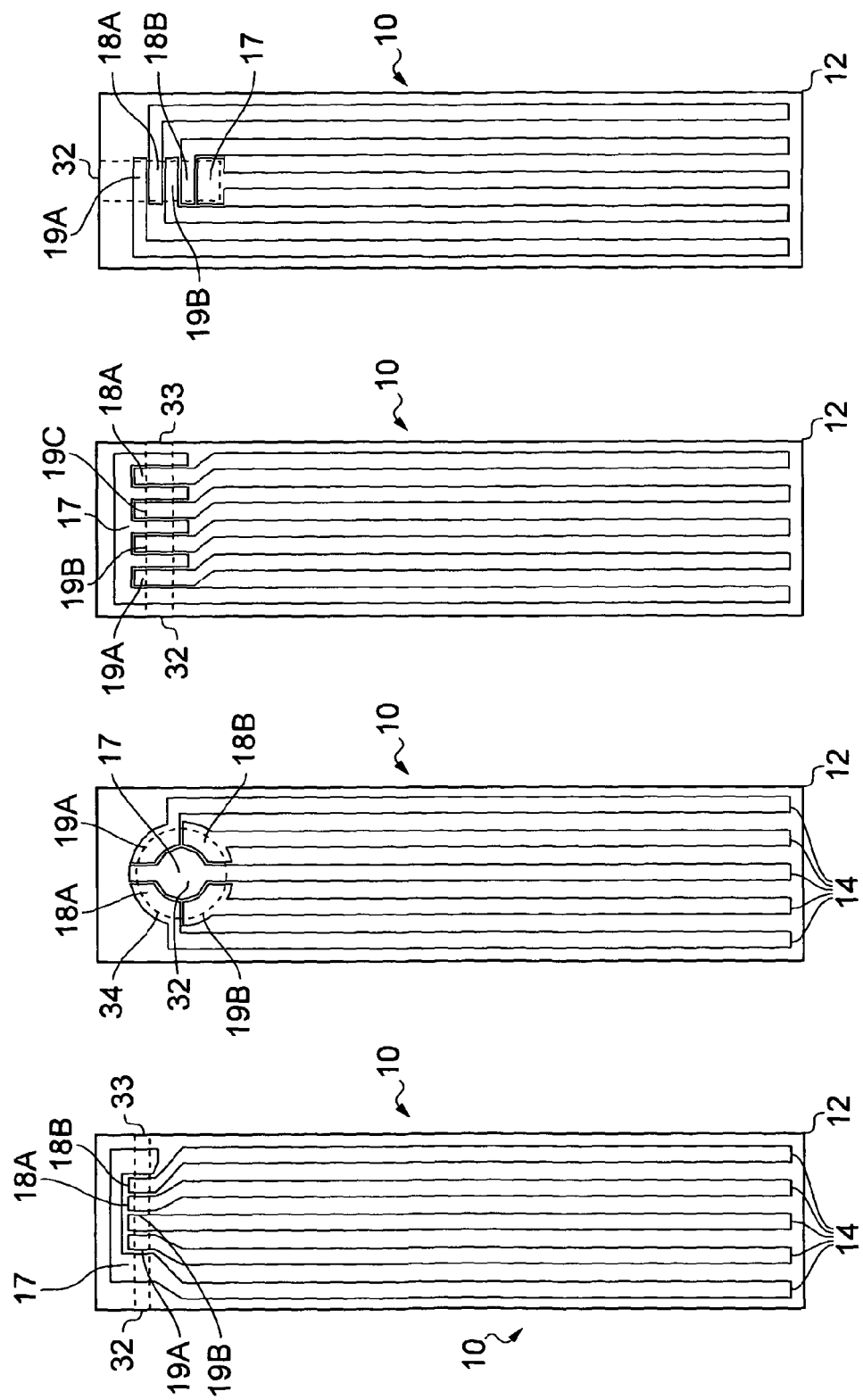
FIG. 22 shows plan views of alternative electrode configurations, which can be used in one or more aspects of this invention.

FIG. 22A shows a generally rectangular sensor 10 having a generally rectangular substrate 12 and conductive tracks 14 providing measurement electrodes in conjunction with a flow path between fluid entrance 32 and air vent 33. The air vent extends from one long side of the sensor to the other long edge of the sensor. Here two calibration electrodes 19A and 19B are provided upstream of two working electrodes 18A and 18B. Variations in the number and nature of the calibration electrodes and working electrodes can be envisaged from the information disclosed herein. For example, working electrode 18A and 18B may be of the same size or may be of different sizes. Furthermore, these may be located next to one another on the flowpath or may be separated by one or more calibration electrodes. The calibration electrodes 19A, 19B may have the same analyte as the analyte of interest thereon or may have a different analyte thereon or both. The calibration electrodes may be next to one another on the flow path or maybe spaced apart by one or more counter and/or working electrodes.

In one embodiment of the invention one or more calibration electrodes are located upstream of one or more working electrodes. In one exemplary embodiment all the calibration electrodes provided are upstream of at least one working electrode. Alternatively or in addition, all the working electrodes provided are downstream of one or more calibration electrodes. Alternatively or in addition, all the calibration electrodes provided lie upstream of all the working electrodes provided. There may be the same calibration analyte on all the calibration electrodes where more than one are provided with or there may be different calibration analytes. There may be different amounts of calibration analyte on each of the calibration electrodes provided or there may be different amounts on the calibration electrodes.

FIG. 22B shows an alternative arrangement in which a fluid entrance 32 is provided above a counter reference electrode 17 located in the centre of four circumferentially arranged measurement electrodes. The four circumferentially arranged measurement electrodes are opposing working electrodes 18A and 18B and opposing calibration electrodes 19A and 19B. A circular spacer has an inner wall 34 to provide the sample chamber. An air vent is also provided (not shown). In this embodiment, a dry reagent layer or film is provided adjacent in close proximity to the calibration analyte on calibration electrodes 19A and 19B. This example does not include the aspect of the invention in which the flow path calibration electrode lies upstream of at least one working electrode on the flow path.

In FIG. 22C, four measurement electrodes are provided, here, three calibration electrodes 19A 19B and 19C are upstream of a single working electrode 18A. Counter reference 17 is an interdigitated electrode having fingers extending in between each of the measurement electrodes 19A, 19B, 19C and 18A. A flow path is provided between fluid entrance 32 and air vent 33.

FIG. 22D shows an alternative to the side fill arrangements of FIGS. 22A and 22C and the top fill arrangement of FIG. 22B. The sensor of FIG. 22D is an end fill having a fluid entrance 32 along the short edge of the sensor 10. Here a calibration electrode 19A lies upstream of a working electrode 18A which lies upstream of a second calibration electrode 19B which lies upstream of a second working electrode 18B. All of these electrodes lie upstream of counter reference electrode 17. An air vent would be provided in chamber lid 30 (not shown).

The time for a signal to be developed at the calibration electrode equals the time for the wave front to reach the calibration electrode plus the time for dissolution of the reagent plus the time for dissolution of the calibration analyte plus the time of the reaction and diffusion of the reaction products to the calibration electrode surface. The time for the signal to be developed at a first working electrode equals the time for the wave front to reach the first working electrode plus the time for dissolution of the reagent plus the time for the reaction plus the time for plus time for diffusion of the reaction products to the electrode surface.

The time for a signal to be developed at a working electrode due to reaction at a calibration electrode equals the time for the wave front to reach the calibration electrode plus the time for dissolution of the reagent plus the time for dissolution of the calibration analyte plus the time of the reaction plus the time for diffusion of reaction products from the calibration electrode to the working electrode surface.

Thus, the time of the assay i.e. the time point at which the measurement of current indicative of analyte concentration should be taken is longer than the time for the signal to be developed at working electrode or calibration electrode and shorter than the time for the diffusion of reaction products from a calibration electrode to the nearest measurement electrode. Thus the time of the assay is constrained by the time for diffusion of reaction products from the calibration electrode to the neighbouring downstream working electrode. Thus, the time for diffusion from the calibration electrode to the next working electrode should be greater than the time of the assay. By placing constraints on the geometrical design of the test strip in accordance with the invention it becomes possible to select a time of assay somewhere in the region of 4 to 10 seconds, perhaps 4 to 6 seconds, perhaps 5 seconds.

Referring now to FIG. 23 a variety of sample entry configurations are possible such as: "Shelf-fill": "End-fill": (requires film to be fastened down to prevent sample entering beneath film): "Top-fill". Many alternative electrode configurations can be used for this invention. FIG. 23 shows cross-sectional views of three example sample entry configurations. Firstly, a shelf fill is shown in which reagent film 40 extends to approximately the outermost edge of substrate 12 and a blood drop fluid drop 52 is placed thereon, adjacent fluid entrance 32. Fluid is drawn through capillary channel 36 along flow path 23 by capillary action. Fluid encounters electrode 17 then first measurement electrode E1 here a working electrode 18A. Fluid next encounters measurement electrode E2 here a calibration electrode 19A having a predetermined amount of calibration analyte 38 thereon. Next fluid encounters a second calibration electrode 19B. Next the fluid encounters a second working electrode 18B before finally arriving at counter reference electrode 17 on measurement electrode E5. One optional variation of the invention is to provide a block, stopper or otherwise to fill in the gap between substrate 12 and reagent film 40 so that blood does not wick underneath reagent film 40.

In the end fill embodiment the chamber lid 30 extends to the very end of substrate 12. Here the conductive layer 13 has been provided with an extra pattern all the way to the edge of substrate 12 to provide a stopper between reagent film 40 and substrate 12. Alternatively an adhesive 54 is provided to secure reagent film 40 to substrate 12 at the edge and so prevent wicking of blood underneath the reagent layer. This is particularly important in an end fill device such as this. Blood wicks through chamber 36 in the direction from fluid entrance 32 to air vent 33 along flow path 23. The fluid encounters a first working electrode 18A and a second working electrode 18B.

Fluid first encounters working electrode 18A followed by two calibration electrodes 19A and 19B and then second working electrode 18B.

A top fill design is also shown in which a blood drop 52 enters through a fluid entrance 32 in chamber lid 30. Air vents 33 are provided at the outer rim of chamber lid 30. Here the fluid first encounters calibration electrodes 19A and 19A' as it spreads out either side to side in a linear sensor or radially in a circular sensor. Fluid then encounters working electrode 18A and 18A' before arriving at counter reference electrode 17.

Various examples will now be described.

EXAMPLES

Example 1

In one embodiment a reagent solution from which a water soluble film could be cast was made containing the following ingredients:

| Ingredient | ~% (w/w) |
|---|---|
| Citrate buffer (20 mM, pH 6) | 68 |
| Carboxymethylcellulose (low viscosity) Sigma, UK, C5678 | 6 |

-continued

| Ingredient | ~% (w/w) |
|---|---|
| Polyvinyl acetate, Sigma, UK, 363081 | 5 |
| Prosolv SMCC ® 50, JS Pharma | 6 |
| Potassium ferricyanide, Sigma UK, 393517 | 14 |
| Glucose oxidase, Biozyme, UK, G03A | 1 |
| Triton ® X-100 | 0.05 |

Numerous formulations have been described for making rapidly dissolving water soluble films and any could be appropriate for this invention and it is not intended to restrict the invention to this single example.

A film is cast from the reagent solution by spreading a thin layer on a smooth plastic substrate and drying it at 50° C. for 15 minutes. The resulting film is cut into strips and may be stored desiccated until used to make test strips.

A device using the above formulation can be manufactured as follows and is described in reference to FIG. 10A and FIG. 10B. Multiple electrodes E1 to E5 are formed on a base substrate 12. The substrate material can be any suitable insulating material. These conductive electrodes can be of the same or different suitable materials. Typically, they are graphite, gold, palladium or platinum. An insulating layer 16 is then applied to cover all of the conductive elements except the contacts and electrode areas. An internal calibration dose of glucose 38 in buffer is applied to one or more of the electrodes. The dry film 40 containing the active ingredients is then applied to cover all the electrodes. In this example, the sample chamber is formed by the application of two spacers 34 which form the 'walls' of the chamber and the application of a hydrophilic film 30 completes the ceiling of the chamber. The sample chamber may be 'pre-formed' before application to the test strip.

The results of testing strips made as described with a buffer solution are shown in FIG. 16 and FIG. 17. The current measured from each measurement area is displayed against time since the device was filled with the sample. FIG. 16 shows the result when the upstream electrode E1 is dosed with glucose. Due to the speed of the assay and the proximity of the standard glucose dose to the measurement electrode no carry over from the upstream glucose dosed electrode is seen. The ability to position the internal standard or standards upstream from other detection areas without seeing any carry over from the upstream areas allows much more flexibility in test strip design and in potentially allowing the measurement areas to all lie within a single sample chamber means a simpler, more cost effective and lower sample volume design can be used when compared to multi channel designs. FIG. 17 shows the results when two electrodes E1 and E4 have been dosed with different amounts of glucose.

The example described allows the measurement of the analyte and multiple internal standards within 5 seconds, i.e. the same time as typical commercial assay systems.

Example 2

An example embodiment comprises a reagent formulation of the following composition. Numerous formulations have been described for making dissolving water soluble films and any could be appropriate for this invention and it is not intended to restrict the invention to this single example.

| Ingredient | ~% w/w |
| --- | --- |
| Citrate buffer (pH 6) | 69 |
| Polyvinylpyrolidone-vinylacetate | 0.7 |
| Dow Corning ® 1500 antifoam | 0.2 |
| Natrosol ® 250 M | 1.4 |
| Prosolv SMCC ® 50 | 13.8 |
| Potassium ferricyanide | 13.8 |
| Glucose oxidase | 1 |

A device using the above formulation can be manufactured as follows. Electrodes are formed on a base substrate. The substrate material can be any suitable insulating material. These conductive electrodes can be of the same or different suitable materials. Typically, they are graphite, gold, palladium or platinum. An insulating layer is then applied to cover all of the conductive elements except the contacts and electrode areas. A reagent film is then applied over the exposed electrode surfaces. The formulation and/or production process of the reagent film may be suitable for screen printing. This formulation may be screen printed onto a release membrane such as release paper and then lifted off to form a reagent film. In this example, the sample chamber is formed by the application of two adhesive pads which form the 'walls' of the chamber and the application of a hydrophilic film completes the ceiling of the chamber. Another method might be to use a 'pre-formed chamber' to achieve better sample chamber volume control in high-volume manufacturing.

The reagent film described herein is non-conductive and in contrast to U.S. Pat. No. 6,241,862 (MCALEER et al) no membrane with openings or pores is retained at the electrode surface on sample introduction as this could hinder the diffusion of the species participating in the analytic reaction. Equally due to rapid dissolution little or no exclusion of red cells takes place. Exclusion of red cells is described in U.S. Pat. No. 6,241,862 (MCALEER et al). In one example embodiment, the present invention is concerned with achieving very rapid dissolution of the reagent film into the sample.

Example 3

This example will describe preparation of a water soluble dry reagent film in accordance with the invention and the construction of a test sensor in accordance with the invention.

First a solution A is prepared as described below.

Solution A—Ingredients and Method 5 g sodium carboxymethycellulose (Blanose 7LF, Ashland Aqualon Functional Ingredients) was mixed with 6 g hydroxypropyl methylcellulose (Methocel E5 Premium LV, Colorcon Ltd) and added to 100 g 20 mM citrate buffer pH 5.8. The solution was then degassed under vacuum.

Film Preparation

Then to make the reagent film, 3 g potassium ferricyanide and 0.4 g glucose oxidase were added to 17 g Solution A and mixed until dissolved.

Approx. 2 ml of reagent solution were placed onto a silicone mat and a No. 6 K-bar (RK Print Coat Instruments Ltd) used to draw out a film of 60 µm wet film thickness. The film was then dried at 50° C. for 10 minutes. The film can then be peeled off the silicone mat and cut to the desired shape for test strip construction. It may also be stored for future use, optionally in the presence of a desiccant.

Sensor Construction

A suitable sprayable adhesive such as Spray-Mount™ (3M) is then sprayed through a mask to coat areas 39 in FIG. 13 in a thin layer of adhesive. The reagent film 40 is then attached to the strip by smoothing it over the adhesive coated areas.

Next a spacer layer 34 is applied to define the walls of the sample chamber 36. The spacer layer 34 can be formed using double sided tape and is between 50 µm and 200 µm thick. Finally, a top layer of hydrophilic film 30 is applied to form the roof of the sample chamber.

Measurement

To use the test strip a portable instrument (not shown) such as a portable test meter applies a constant potential of approximately 400 mV between the counter reference electrode E5 and each of the four working electrodes E1 to E4. This potential is sufficient to oxidise any reduced mediator at the working electrode surfaces. The current flowing at each working electrode is independently measured at a given time after the initiation of the assay. The assay timing could be initiated from sample being detected at one of the working electrodes or at each working electrode independently. The time of the assay is preferably less than 10 seconds and most preferably 5 seconds or less.

Current transients measured at a single working electrode that has no additional dose of glucose on its surface in a strip of the current invention are shown in FIG. 14. The transients are shown for different levels of glucose in a buffer sample.

If buffer with no glucose in is used as the sample then the transient responses of E1, E2, E3 and E4 are shown in FIG. 15 where E1, E2 and E4 have no glucose dose but E3 has had a deposit of glucose solution dried on it prior to strip assembly. There is no evidence of any additional glucose being measured on the downstream electrode (E4 in this case).

It is possible for the internal standard electrode to be upstream of the electrode used to measure unadulterated sample. This is because the assay times are quick enough for there not to be enough time for any glucose (or products of the enzyme reaction) from the predetermined dose to dissolve and diffuse to any detection area other than that on which it was deposited.

Example 4

Internal Standard Correction of Glucose Measurement

An error free working electrode current can be derived from Equation 1 and 2 as described above $$S=(E1-E2)/i_s=(E1c-E2c)/i_s \qquad \text{Equation 1}$$

$$i_m=i_s(E2-E3)/(E1c-E2c) \qquad \text{Equation 2}$$

In this example a 20% slope error (S=1.2) and 3 µA background current were assumed to apply to what should have been a current reading of 12 µA. The internal standard was assumed to have an expected response of 10 µA. In this example the responses from the three electrodes described above are:

E1=29.4 µA

E2=17.4 µA

E3=3 µA

Following the correction process above:

E2c=17.4−3=14.4 µA

E1−E2=12 µA so

S=(E1−E2)/$i_s$=12/10=1.2 therefore as we know that $i_m$=(E2−E3)/S=E2c/S $i_m$=E2c/1.2=14.4/1.2=12 µA.

In an exemplary embodiment this corrected working electrode current can then be used in a calibration graph such as that shown in FIG. 5 to derive a corrected measurement result indicative of the amount of analyte in the sample (STEP 370). Alternatively, FIG. 5 may be used initially on the measured currents to derive corresponding glucose results, and the glucose results corrected in a corresponding way to that shown above to derive a corrected measurement result indicative of the amount of analyte in the sample.

The present invention relates to a sensor device for the measurement of clinically relevant analytes and optionally a disposable sensor device. The invention is illustrated in an example embodiment through a device for measurement of blood glucose levels and in particular in the description of a glucose test strip with an internal standard comprising a calibration analyte, the strip containing reagents in a highly soluble dry film. Variations and modifications to this will be apparent to those skilled in the art and these variations and modifications are intended to be covered by this invention. For example, although a strip is one embodiment of the invention, the invention is applicable to other forms of test sensor than a strip. Likewise although the example fluid used is blood the invention can be used for other fluids, particularly body fluids, such as blood, plasma, urine, interstitial fluid, saliva, spinal fluid.

Where a film is described, a film having two opposed, generally planar, generally parallel sides, the film may be of the same order of size of area as a measurement electrode or it may be a few times larger in area or it may be significantly larger. Thus a small reagent film may comprise a disc or dot of reagent of any suitable shape of roughly the same size in area as a measurement electrode. The reagent film may be generally rectangular. The reagent film may be sized to cover two or more, or all measurement electrodes. In one optional embodiment which is less preferred in which dry reagent not in the form a film is used, the reagent may be in the form of a 3 dimensional drop having dimensions in the x, y and z directions of about the same order as one another and, optionally, about the same order as a width or length as a measurement electrode.

Although the invention is described in terms of a glucose electrochemical test strips, an internal standard test sensor for other analytes could also be created according to this invention by use of suitable reagents such as enzymes and mediators. Examples of other possible analytes include: cholesterol, triglycerides, lactate, proteins, pyruvate, alcohol, uric acid or ketones. Examples of possible analytes and possible reagents such as enzymes and mediators and possible co-factors are known to those skilled in the art and from the patent documents enumerated herein and these are to be included as aspects to the present invention.

Thus, one application where control of reagent concentration becomes critical is the use of an internal standard measurement where the standard is present in or in close contact with the reagent of one or more electrodes. Without good control over the dissolution of the internal standard and the reagents a reliable control measurement would be impossible to achieve. Rapid reagent dissolution into the sample is one way to achieve good dissolution control. If initial reagent dissolution is fast enough then the sample becomes homogeneous more quickly than with a reagent formulation that is initially slow to rehydrate and dissolve. This is most likely to be the case with reagent layers designed to remain as a hydrated membrane for the duration of the assay.

Such an internal standard should preferably be a measurement of a known quantity of exactly the analyte being measured in the same sample. The detailed assay of the internal standard should resemble that of the analyte as closely as possible. In systems that rely on sample flow to 'collect' and mix the standard there is a high risk that this dissolution and flow is not consistent enough to provide an accurate standard reading. Preferably the internal standard comprising a calibration analyte, which may itself be glucose, is as close as possible to the signal measurement area i.e. close to the measurement electrode.

The use of a water soluble, reagent containing dry film is described in one example embodiment. When used in conjunction with an internal calibrant, the dry film allows the internal calibrant to be identical to the analyte and reagent layer to be placed adjacent to each other and adjacent to the measurement area of the test strip. This allows measurement of the internal calibrant to be done quickly and without seeing any signal carry over to nearby measurement areas in the same sample flow path In one exemplary embodiment of one aspect of the present invention it is therefore an object of this invention to describe the use of a rapidly water soluble pre-formed dry film containing the active ingredients for the test strip. This film can be applied on top of the measurement electrode of the strip which may also have been dosed with an internal calibrant. Such a film can be applied over multiple electrodes in the same sample chamber. A different level of calibrant may be applied to different electrodes to create a multi-level internal calibration.

In one exemplary embodiment of one aspect of the present invention a disposable electrochemical sensor for the detection of an analyte such as glucose in a liquid sample is provided in which the reagent is applied in the form of a water soluble dry film such as those more typically utilised for the oral administration of pharmaceuticals or breath freshening compounds (e.g. U.S. Pat. No. 5,948,430). One exemplary embodiment of the present invention has multiple measurement areas within the sample chamber and an internal standard dose of glucose added prior to application of the dry reagent film.

It is therefore one object of one embodiment of this invention to describe a water soluble dry reagent film designed to display rapid hydration and dissolution into the sample. Rapid dissolution results in sensitivity to the analyte of interest and calibration analyte in close proximity thereto at extremely short times after sample introduction. In one embodiment of the present invention there is provided an electrochemical diagnostic test strip that includes one or more internal standards. In one embodiment the invention provides an internal standard within a sensor device that can be assembled from essentially dry components. The components are sufficiently dry or free from liquid or moisture so that no appreciable reaction can take place when these are placed adjacent one another.

One or more embodiments of the present invention are provided with one or more of the following:
multiple measurement electrodes in a single sample flow path;
a highly water soluble film containing the assay reagents that is positioned within the sample chamber
the film containing the assay reagents is on the same side of the chamber as the measurement electrodes
a known dose of analyte deposited on the surface of one or more of the detection electrodes.
the analyte dosed electrode may be upstream of other undosed electrodes.

film dissolution is quick enough to allow a test time of less than 10 sec.

film dissolution is slow enough for the strip to fill without washing the reagents to one end of the sample chamber to an extent that affects the glucose response from each detection electrode.

the reagent containing film is placed in position during strip manufacture in an essentially dry state.

Thus, the film described in one embodiment of this invention is readily soluble in the presence of the sample so that release and reaction of the assay reagents occurs in a time compatible with the desired total test time and/or the filling time of the sensor.

The present invention seeks to use an internal standard(s) to measure total error on the same test strip and in the same sample as that being tested. This method does not need to know where the source of error is coming from or make assumptions about whether a particular sample will behave in a typical way. The internal standard method relies on the accuracy of the internal standard measurement. Error in the internal standard may be reduced by the use of multiple standards with the same or different amounts of analyte. Also the measurement of the internal standard dose of analyte should preferably mimic as closely as possible the measurement of the sample analyte. It is therefore better to use a predetermined dose of the test analyte rather than a different internal standard. It is also not desirable for the assay to require the internal standard dose of analyte to have to travel significantly further to be detected than the analyte in the sample. It is also desirable that, none of the other important features of test strip design such as sample volume and test time should be compromised in the design of a test strip containing an internal standard. In one embodiment of the invention the calibration analyte forming the internal standard should react with the reagents in as similar way as possible to the sample analyte to provide the best possible calibration information.

In contrast to the prior art, one or more embodiments of this invention rely on the formation of a dry film of reagent which is optionally, subsequently applied over the electrode surfaces, at least one of which is provided with a calibration analyte in dry form. This use of a dry film assists in reducing reaction between the reagents and the standard dose of analyte applied onto one or more of the electrode surfaces. Furthermore, this subsequent placing of the dry film also assists in reducing reaction between the reagents and the standard dose of analyte applied on to one or more of the electrode surfaces.

In one embodiment of the invention in the use of multiple standards, each subsequent measurement electrode is not measuring the sum of the standard analyte amounts before it. This can simplify the mathematics used in determining the actual calibration current from each calibration electrode. Each internal standard is independent of the others because the assay times are quick enough for there not to be enough time for any glucose from the predetermined dose to dissolve and diffuse to any detection area other than that on which it was deposited. In this way the optimal arrangement of unadulterated sample detector and internal standard measurement electrode(s) can be determined experimentally rather than an arrangement being dictated by sensor design.

Some of the key benefits of one or more embodiments of the present invention include the following. The predetermined amount of calibration analyte present in the sensor is substantially prevented from reacting with the sensor reagents during sensor manufacture and/or storage to any appreciable extent in the present invention. The close proximity of the glucose dose adjacent to the reagent film means very short and similar transport distances for the products of the reaction with the dosed analyte and the sample analyte. This leads to the ability to use short assay times which means cross over between measurement electrodes is reduced or effectively eliminated and the assay can be run in a single sample channel. This leads to a simplified design compared to multi-channel options and allows the sample volume to be kept lower than would be required to fill multiple channels.

Therefore, a test strip with the benefits of an internal standard based self-calibration can be produced without compromising the key features of test time and sample volume.

Although described with specific reference to a glucose sensor the invention is also applicable to other diagnostic tests requiring internal calibration. Thus, whilst specific embodiments of the present invention have been described above, it will be appreciated by those skilled in the art that departures from the described embodiments may still fall within the scope of the present invention as afforded by the claims.

The invention claimed is:

1. An electrochemical sensor device for measuring a level of an analyte of interest in a fluid comprising:
   a flowpath for a fluid;
   a substrate on one side of the flowpath;
   on the substrate, a calibration electrode comprising:
   i) a first layer comprising a first measurement electrode;
   ii) a second layer located on the first layer, the second layer comprising an internal standard comprising a first predetermined amount of first dry calibration analyte; and
   iii) a third layer located on the second layer, the third layer comprising a dry reagent film layer comprising a reagent for the analyte of interest,
   wherein at least part of the third layer comprising the dry reagent film layer overlays at least part of the second layer comprising the first predetermined amount of the first dry calibration analyte located on the first layer comprising the first measurement electrode to form the calibration electrode; and
   wherein a distance between at least part of the dry reagent film layer and at least part of the first predetermined amount of the first dry calibration analyte is within about 15 µm.

2. A device according to claim 1, in which the first dry calibration analyte and the analyte of interest are the same analyte.

3. A device according to claim 1, in which the dry reagent film layer comprises a dry film having two exposed opposing, generally parallel, generally planar surfaces prior to being located on the second layer to form the dry reagent film layer.

4. A device according to claim 1, in which the dry reagent film layer comprises a water soluble dry film having two, opposing, generally parallel, generally planar surfaces.

5. A device according to claim 4, wherein the dry reagent film layer is in physical contact with the first predetermined amount of first dry calibration analyte.

6. A device according to claim 1, in which the dry reagent film layer comprises a water soluble dry film having two exposed opposing, generally parallel, generally planar surfaces.

7. A device according to claim 1, wherein a distance between at least part of the dry reagent film layer and at least part of the first predetermined amount of the first dry calibration analyte is within about 10 μm.

8. A device according to claim 1, wherein a distance between at least part of the dry reagent film layer and at least part of the first predetermined amount of the first dry calibration analyte is within about 5 μm.

9. A device according to claim 1, in which the dry reagent film layer is in physical contact with the first predetermined amount of the first dry calibration analyte.

10. A device according to claim 1, in which the dry reagent film layer is in the form of water soluble dry film having two exposed opposing, generally parallel, generally planar surfaces, and at least part of the water soluble dry film (i) overlays at least part of the first predetermined amount of first dry calibration analyte to form the dry reagent film layer having one exposed surface, or (ii) overlays at least part of the first predetermined amount of first dry calibration analyte and at least part of the first measurement electrode to form the dry reagent film layer having one exposed surface.

11. A device according to claim 1, further comprising:
a second measurement electrode;
wherein the second measurement electrode is free from calibration analyte;
wherein the dry reagent film layer comprises a dry film having two exposed opposing, generally parallel, generally planar surfaces prior to being located on the flowpath, the dry film located on the second measurement electrode to form a first working electrode free from calibration analyte.

12. A device according to claim 11, wherein the calibration electrode lies upstream of the first working electrode.

13. A device according to claim 11, further comprising a second working electrode, the second working electrode comprising:
a third measurement electrode free from calibration analyte; and
a portion of the dry reagent film layer, wherein the portion of the dry reagent film layer is located on the third measurement electrode.

14. A device according to claim 11, wherein the flowpath is a single flowpath or a single linear flowpath, further comprising a component that is configured to provide an assay time for a measurement at one of the first and second measurement electrodes that is less than the time it takes for diffusion of reagent or reaction products from the other of the first and second measurement electrodes, wherein the component is selected from the group consisting of one or more of: a geometry of the flowpath, a height of the flowpath, a width of the flowpath, a length of the flowpath, a location along the flowpath of at least the first measurement electrode, a location along the flowpath of the second measurement electrode, a distance between the first and second measurement electrodes, a dissolution rate of the reagent, a dissolution rate of the first predetermined amount of the first dry calibration analyte, and a thickness of the dry reagent film layer.

15. A device according to claim 1, further comprising:
a first working electrode comprising:
a second measurement electrode free from calibration analyte; and
a portion of the dry reagent film layer comprising the reagent for the analyte of interest,
wherein the calibration electrode lies upstream of the first working electrode.

16. A device according to claim 15, wherein the flowpath is a single flowpath or a single linear flowpath.

17. A device according to claim 1, further comprising:
a first working electrode, the first working electrode comprising a second measurement electrode free from calibration analyte having the dry reagent film layer for the analyte of interest thereon to form the first working electrode,
wherein the calibration electrode and the first working electrode are located on the flowpath,
wherein the flowpath is a single flowpath or a single linear flowpath, and
a component configured to enable a suitable measurement indicative of the concentration of the analyte of interest to be taken at the first working electrode before first dry calibration analyte or reaction products from the calibration electrode can travel by diffusion or otherwise from the calibration electrode to the first working electrode, wherein the component is selected from a group consisting of one or more of:
a geometry of the flowpath, height of the flowpath, a width of the flowpath, a length of the flowpath, a location along the flowpath of at least the calibration electrode, a location along the flowpath of at least the first working electrode, a distance between the calibration electrode and the first working electrode, a dissolution rate of the reagent, a dissolution rate of the predetermined amount of the first dry calibration analyte, and a thickness of the dry reagent film layer.

18. A device according to claim 1, in which the dry reagent film layer is in the form of a water soluble dry reagent film having two exposed opposing, generally parallel, generally planar surfaces prior to being located on the flowpath, the dry reagent film comprising:
a first film forming ingredient; and
a first active ingredient sensitive to the analyte of interest.

19. A device according to claim 18, the dry reagent film comprising a first film forming ingredient selected from the group of a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose.

20. A device according to claim 19, the dry reagent film further comprising a second film forming ingredient selected from a polymer, a modified starch, pulluan, hydroxethyl cellulose, hydroxypropyl cellulose, polyvinyl pyrrolidone, polyvinyl pyrrolidone vinyl acetate, polyvinyl alcohol, sodium alginate, natural gums, water dispersible polyacrylates, sodium carboxymethyl cellulose and hydroxyl propyl methyl cellulose.

21. A device according to claim 18, further comprising a first film forming ingredient and a second film forming ingredient; the second film forming ingredient having better dissolution and less hydrophobic properties than the first film forming ingredient.

22. A device according to claim 18, further comprising at least one further film forming ingredient selected from the group consisting of: a plasticizer, a disintegrant, and a surfactant.

23. A device according to claim 22, wherein the at least one further film forming ingredient is a plasticizer, and wherein the plasticizer is selected from the group consisting of: xylitol, sorbitol, erythritol, and polyethylene glycol.

24. A device according to claim 22, wherein the at least one further film forming ingredient is a disintegrant, and wherein the disintegrant is selected from the group consisting of: microcrystalline cellulose, sodium croscarmellose, and sodium starch glycate.

25. A device according to claim 1, further comprising a second measurement electrode and a third measurement electrode, wherein the dry reagent film layer comprises a dry film having two opposing, generally parallel, generally planar surfaces, and wherein the dry film extends between and is located on at least two of the first, second, and third measurement electrodes.

26. A device according to claim 25, wherein the dry film extends between and is located on all of the first, second, and third measurement electrodes.

27. An electrochemical sensor device for measuring a level of an analyte of interest in a fluid comprising:
   a sample chamber comprising a flowpath for the fluid and a substrate;
   on the flowpath, a calibration electrode, comprising:
   i. a first measurement electrode on the substrate,
   ii. a dry reagent film layer comprising a reagent for the analyte of interest, and
   iii. an internal standard comprising a first predetermined amount of a first dry calibration analyte located on the first measurement electrode,
      wherein at least part of the dry reagent film layer is located on at least part of the first predetermined amount of first dry calibration analyte located on the first measurement electrode, to form the calibration electrode and,
      wherein a distance between at least part of the dry reagent film layer and at least a part of the first predetermined amount of first dry calibration analyte is within about 15 μm.

28. A device according to claim 27, further comprising a second measurement electrode and a third measurement electrode, wherein the dry reagent film layer comprises a water soluble dry film having two exposed opposing, generally parallel, generally planar surfaces prior to being located on the flowpath, and wherein the water soluble dry film extends between and is located on at least two of the first, second, and third measurement electrodes.

29. A device according to claim 28, wherein the water soluble dry film extends between and is located on all of the first, second, and third measurement electrodes.

30. A device according to claim 27, wherein a distance between at least part of the dry reagent film layer and at least part of the first predetermined amount of the first dry calibration analyte is within about 10 μm.

31. A device according to claim 27, wherein a distance between at least part of the dry reagent film layer and at least part of the first predetermined amount of the first dry calibration analyte is within about 5 μm.

* * * * *